United States Patent [19]

Mishra et al.

[11] Patent Number: 6,150,824
[45] Date of Patent: Nov. 21, 2000

[54] CONTACTLESS SYSTEM FOR DETECTING SUBTLE SURFACE POTENTIAL CHARGE PATTERNS

[75] Inventors: Satchidanand Mishra, Webster; Edward A. Domm, Hilton, both of N.Y.; Zoran D. Popovic, Mississauga, Canada; Denis C. Thomas, Hilton, N.Y.; Samy A. Mesbah, Mississauga, Canada; Dennis J. Prosser, Walworth; Steven P. Nonkes, Webster, both of N.Y.

[73] Assignee: Xerox Corporation, Stamford, Conn.

[21] Appl. No.: 08/961,061

[22] Filed: Oct. 30, 1997

[51] Int. Cl.⁷ .................................................. G01N 27/60
[52] U.S. Cl. ...................... 324/452; 324/456; 324/457; 399/73
[58] Field of Search .............................. 399/73; 324/109, 324/111, 134, 102, 456, 457, 458, 452

[56] References Cited

U.S. PATENT DOCUMENTS

| | | | |
|---|---|---|---|
| 3,729,675 | 4/1973 | Vosteen | 324/72 |
| 3,898,001 | 8/1975 | Hardenbrook et al. | 355/3 R |
| 4,134,137 | 1/1979 | Joacobs et al. | 358/293 |
| 4,305,132 | 12/1981 | Tsuboshima | 324/111 |
| 4,318,042 | 3/1982 | Eda et al. | 324/72.5 |
| 4,367,948 | 1/1983 | Suzuki | 355/14 |
| 4,683,436 | 7/1987 | Suzuki | 324/458 |
| 5,065,102 | 11/1991 | Takanashi et al. | 324/452 |
| 5,175,503 | 12/1992 | Mishra et al. | 324/452 |

OTHER PUBLICATIONS

Z.D. Popovic, D. Parco and P. Iglesias, SPIE vol. 1253 Hard Copy and Printing Materials, Media and Processes, 175 (Jan. 1990).

Zoran Popovic, Pablo Iglesias, "Characterization of Microscopie Elelectrical Non–Uniformities in Xerographic Photoreceptors", Fifth International Congress on Advances and Non–Impact printing Technologies, Nov. 12–17, 1989, San Diego, Calif.

Zoran Popovic, Dave Parco, Pablo Iglesias, "Nature of Microscopic Electrical Defects in organic Photoreceptors", proceedings SPIE–SPSE Electronic Imaging Science and Technology Symposium, Feb. 11–16, 1990, Santa Clara, Calif.

R. Gerhard–Multhaup and W. Perry, J. Phys. E; Sci. Instrum. 16, 421–422 (Jan./1983).

E.J. Yarmchuck and G.E. Keefe, J. Appl. Phys 66 (11), Dec. 1, 1989.

*Primary Examiner*—Safet Metjahic
*Assistant Examiner*—Jose M. Solis

[57] ABSTRACT

A contactless process for detecting electrical patterns on the outer surface of a member comprising providing a member having a charge pattern on an outer surface, repetitively measuring the charge pattern on the outer surface of the member with an electrostatic voltmeter probe maintained at a substantially constant distance from the surface, the distance between the probe and the imaging member being slightly greater than the minimum distance at which Paschen breakdown will occur to form a parallel plate capacitor with a gas between the probe and the surface, the frequency of repetition being selected to cause all time dependent signals to fall out of phase by a predetermined amount, and averaging the out of phase time dependent signals over a sufficient number of measuring repetitions to eliminate the time dependent signals. In one embodiment, the contactless process detects surface potential charge patterns in an electrostatographic imaging member. Apparatus for carrying out these processes are also described.

16 Claims, 11 Drawing Sheets

CONTACTLESS SYSTEM FOR DETECTING SUBTLE SURFACE POTENTIAL CHARGE PATTERNS

BACKGROUND OF THE INVENTION

This invention relates in general to electrostatography and, more specifically, to apparatus and process for detecting subtle surface potential charge patterns on the outer surface of members.

In the art of xerography, a xerographic plate or photoreceptor comprising a photoconductive insulating layer is imaged by first uniformly depositing an electrostatic charge on the imaging surface of the xerographic plate and then exposing the plate to a pattern of activating electromagnetic radiation such as light which selectively dissipates the charge in the illuminated areas of the plate while leaving behind an electrostatic latent image in the non-illuminated areas. This electrostatic latent image may then be developed to form a visible image by depositing finely divided electroscopic marking particles on the imaging surface.

A photoconductive layer for use in xerography may be a homogeneous layer of a single material such as vitreous selenium or it may be a composite layer containing a photoconductor and another material. One type of composite photoconductive layer used in electrophotography is illustrated in U.S. Pat. No. 4,265,990, the entire disclosure thereof being incorporated herein by reference. A photosensitive member is described in this patent having at least two electrically operative layers. One layer comprises a photoconductive layer which is capable of photogenerating holes and injecting the photogenerated holes into a contiguous charge transport layer. Generally, where the two electrically operative layers are positioned on an electrically conductive layer with the photoconductive layer sandwiched between a contiguous charge transport layer and the conductive layer, the outer surface of the charge transport layer is normally charged with a uniform electrostatic charge and the conductive layer is utilized as an electrode. In flexible electrophotographic imaging members, the electrode is normally a thin conductive coating supported on a thermoplastic resin web. Obviously, the conductive layer may also function as an electrode when the charge transport layer is sandwiched between the conductive layer and a photoconductive layer which is capable of photogenerating electrons and injecting the photogenerated electrons into the charge transport layer. The charge transport layer in this embodiment, of course, must be capable of supporting the injection of photogenerated electrons from the photoconductive layer and transporting the electrons through the charge transport layer.

The photoreceptors are usually multilayered and comprise a substrate, an optional conductive layer (if the substrate is not itself conductive), an optional hole blocking layer, an optional adhesive layer, a charge generating layer, and a charge transport layer and, in some belt embodiments, an anti-curl backing layer.

Although excellent toner images may be obtained with multilayered photoreceptors, it has been found that as more advanced, higher speed electrophotographic copiers, duplicators and printers were developed, different imaging characteristics were encountered with photoreceptors fabricated of identical materials but in different fabrication runs. Since photoreceptor properties can vary from one production run to another, copy quality using photoreceptors from different production runs can be very different. This is because in the production of electrophotographic imaging members the complex nature of the manufacturing process renders unpredictable electrical characteristics of the coated photoreceptor from batch to batch and from month to month. For example, alteration of photoreceptor imaging properties can occur due to changes in the manufacturing environment, the installation or adjustment of new coating applicators or the initial use of a newly prepared batch of coating material for one of the many layers of the photoreceptors such as the hole blocking layer, charge generating layer, or charge transport layer. These changes in photoreceptor properties are difficult to identify within a reasonable length of time subsequent to the point in time when the photoreceptor comes off a production line.

One technique for detecting undesirable characteristics in photoreceptors from a specific production run is to actually cycle the photoreceptor in the specific type of copier, duplicator and printer machine for which the photoreceptor was fabricated. Generally, it has been found that actual machine testing provides an accurate way of detecting charge deficient spots in a photoreceptor from a given batch. However, machine testing for detecting nonuniform charging is a very laborious and time consuming process which requires involving hand feeding of sheets by test personnel along with constant monitoring of the final quality of every sheet. Moreover, accuracy of the test results depends a great deal upon interpretations and behavior of the personnel that are feeding and evaluating the sheets. Further, since machine characteristics vary from machine to machine for any given model or type, reliability of the final test results for any given machine model must factor in any peculiar quirks of that specific machine versus the characteristics of other machines of the same model or type. Because of machine complexity and variations from machine to machine, the data from a test in a single machine is not sufficiently credible to justify the scrapping of an entire production batch of photoreceptor material. Thus, tests are normally conducted in three or more machines. Since a given photoreceptor may be used in different kinds of machines such as copiers, duplicator and printers under markedly different operating conditions, detection of problem photoreceptors based on the machine tests of a representative test photoreceptor sample is specific to the actual machine in which photoreceptors from the tested batch will eventually be utilized will not necessarily predict whether the appearance of a problem will occur if the same type of photoreceptor were used in another different type of machine. Thus, for example, a machine charging uniformity test would have to be conducted on each different type of machine. This becomes extremely expensive and time consuming. Moreover, because of the length of time required for machine testing, the inventory of stockpiled photoreceptors waiting approval based on testing in machines can reach unacceptably high levels. For example, a batch may consist of many rolls with each roll yielding thousands of belts. Still further delays are experienced subsequent to satisfactory testing because the webs must thereafter be formed into belts, packaged and shipped.

Voltage variations which can occur on a charged imaging surface of a photoreceptor include charge deficient spots where the voltage sharply drops hundreds of volts along an extremely short lateral distance along the imaging surface of about 10 micrometers to about 100 micrometers. Typical two dimensional lateral sizes of charge deficient spots are on the order of between about 10 micrometers×10 micrometers and about 100 micrometers×100 micrometers. A line graph voltage profile of such a charge deficient spot has the appearance of a long narrow spike extending downwardly from the generally horizontal surface charge profile. Any probe for detecting a charge deficient spot must detect voltage changes over an extremely small area. The shield of the probe for detecting a charge deficient spot must be biased at about the average voltage of the photoreceptor surface to avoid air breakdown and destructive arcing. The resolution of this type of probe depends on the size of the probe electrode and the distance between the probe and the photoreceptor surface, typically very close to the photoreceptor, e.g. 100 micrometers. For measuring charge deficient spots, it is not necessary to have a very precise measurement of background voltage because the main function of background voltage is to bias the shield of a charge deficient measuring probe to prevent arcing.

Another type of voltage variation encountered is one which gradually fluctuates between about 1 to about 2 volts over a lateral distance along the imaging surface of between about 1 to 2 millimeters. A line graph voltage profile of such voltage variation appears as a rippled, substantially horizontal baseline voltage curve. This extremely subtle defect is particularly difficult to rapidly detect and cannot be detected by scanners designed for detecting charge deficient spots. This gradual voltage fluctuation nonuniformity is especially critical for advanced, highly sophisticated superimposed multiple image systems, particularly color imaging systems where at least one toner image is formed over at least one previously formed image and the resulting plurality of developed images are simultaneously transferred to a receiving member to produce full color prints or copies. For example, superimposed multiple electrostatographic image systems involve the formation of an electrostatic latent image on an imaging member, development of the latent image with toner particles to form a toner image, recharging and exposing of the charged imaging member to form a second electrostatographic latent image, and development of the second latent image with a toner having a color different from the previous toner. Additional charge, expose and development steps may be used for still additional colors. The final superimposed colored images are transferred to a receiving member. The photoreceptor coating thickness and deposited charge uniformity requirements for superimposed multiple image systems are extremely stringent and require highly sensitive electronic mapping of charge and thickness of the photoreceptor coating for detection of unacceptable imaging quality characteristics prior to distribution of photoreceptors to customers. The charging uniformity requirements for superimposed colored image systems is on the order of less than 5 volts. In other words, for testing of photoreceptors to be used in high tolerance imaging systems such as superimposed colored image systems, the electronic map of the charged surface of the photoreceptor should be accurate within 1 to 2 volts with a lateral resolution of less than about 1 millimeter. If the charging uniformity of a photoreceptor production batch fails to meet these stringent tolerance requirements, color shifting can occur during imaging which leads to copy quality degradation. Thus, there is a need for an improved system for mapping subtle changes in charge and coating thickness for photoreceptors.

Conventional charging devices such as wire and multi-pin electrode devices are inherently unstable and difficult to use in conducting, with any high degree of precision, scanning measurements for determining the uniformity of deposited charge and thickness of coatings on photoreceptors. Common examples of corona generating elements in a charging device in a xerographic copier or printer are thin wire, multiple pin, saw tooth blade electrodes. The geometry of a corotron is generally rectangular. The walls of the corotron serve as a shield. These corotrons extend across the width of belt photoreceptors or from one end to the other of drum photoreceptors and charge the passing imaging surface of a photoreceptor. It has been found that such corotrons do not produce uniform charging due to local nonuniformity of charging elements in the corotron or electrodynamic instabilities, for example, those exhibited by a saw tooth blade electrode. These electrode elements are also used in a scorotron which has grids of various shapes located at the charging end of the corona generating elements. The grid smoothes out nonuniformity of charging. However, the scorotron operates in a constant voltage mode and therefore covers up and hides nonuniformities in thickness and charge of photoreceptors. These charging devices perform satisfactorily for machines in which the required uniformity levels are of the order of 10 volts. However, these charging devices are unsatisfactory for highly sensitive electronic mapping of charge and thickness of the photoreceptor coating for detection of unacceptable imaging quality characteristics of photoreceptors for advanced, highly sophisticated superimposed colored image machines.

INFORMATION DISCLOSURE STATEMENT

U.S. Pat. No. 5,175,503 to Mishra et al., issued Dec. 29, 1992—A process for ascertaining the projected imaging cycle life of an electrophotographic imaging member is disclosed including the steps of (a) providing at least one electrophotographic imaging member having a cycling life of a known number of imaging cycles, the imaging member comprising an electrically conductive layer and at least one photoconductive layer, (b) repeatedly subjecting the electrophotographic imaging member to cycles comprising electrostatic charging and light discharging steps, (c) measuring dark decay of the photoconductive layer during cycling until the amount of dark decay reaches a crest value, (d) establishing with the crest value a reference datum for dark decay crest value versus imaging cycles, (e) repeatedly subjecting a virgin electrophotographic imaging member to aforesaid cycles comprising electrostatic charging and light discharging steps until the amount of dark decay reaches a crest value which remains substantially constant during further cycling, and (f) comparing the dark decay crest value of the virgin electrophotographic imaging member with the reference datum to ascertain the projected cycling life of the virgin electrophotographic imaging member.

Z. D. Popovic, D. Parco and P. Iglesias, SPIE Vol. 1253 Hard Copy and Printing Materials, Media and Processes, 175 (1990)—A scanning stylus instrument is described for use in the investigation of the electrical properties of individual microscopic defects in organic photoreceptors. A schematic diagram of the measurement circuitry is shown in FIG. 1 on page 176.

Zoran Popovic, Pablo Iglesias, "Characterization of Microscopic Electrical Non-Uniformities in Xerographic Photoreceptors", Fifth International Congress on Advances and Non-impact Printing Technologies, Nov. 12–17, 1989, San Diego, Calif.—An approach to study electrical nonuniformities in photoreceptors is disclosed in which a shielded stylus is used to scan a photoreceptor while in intimate contact with the photoreceptor surface. The photoreceptor is carried on a computer controller X-Y stage. The ground plane of the photoreceptor is connected to the high voltage power supply through a resistor and high voltage relay. A polished stylus tip is brought into contact with the photoreceptor surface. The stylus tip is immersed in silicon oil to prevent electrical breakdown. The presence of silicon oil insulation is absolutely necessary for reproducible measurements. The stylus shield is grounded and the sensing electrode connected to an electrometer to measure the charge flow as voltage is applied to the sample. The whole system is controlled as Xerox 6065 personal computer.

Zoran Popovic, Dave Parco, Pablo Iglesias, "Nature of Microscopic Electrical Defects in Organic Photoreceptors", Proceedings SPIE-SPSE Electronic Imaging Science and Technology Symposium, Feb. 11–16, 1990, Santa Clara, Calif. —The device described in the paper entitled "Characterization of Microscopic Electrical Non-Uniformities in Xerographic Photoreceptors", above, is used to investigate the electrical properties of individual microscopic electrical defects in organic xerographic photoreceptors. The shape of individual microscopic electrical defects were mapped and their current-voltage characteristics were measured.

R. Gerhard-Multhaupt and W. Perry, J. Phys. E; Sci. Instrum. 16, 421–422 (1983).—A scanning capacitive probe is described for the measurement of surface-charge distributions on an electret foils. The probe is a MOSSET electrometer follower together with a high resolution adapter.

E. J. Yarmchuck and G. E. Keefe, J. Appl. Phys. 66 (11), Dec. 1, 1989.—A technique is disclosed for direct, quantitative measurements of surface charge distributions on photoconductors. The photoconductors are carried on a stepping table from a corona charging station to an exposure station and then to the measurement station. Surface charge distribution is determined by a sequence of point-by-point charge measurements at different locations relative to the exposure. Charge measurements are made with an electrometer.

U.S. Pat. No. 3,898,001 to Hardenbrook et al, issued Aug. 5, 1975.—An electrometer system is disclosed which measures electrostatic charges such as a charge level on a photoconductor surface. The electrometer measures a drop in surface voltage in an absence of light on a photoreceptor which is characterized as dark decay, e.g. see Column 1, lines 27–52. The electrometer can measure the remaining or background voltage on a photoreceptor remaining after exposure. The control of this background voltage is important for proper development and copy quality.

U.S. Pat. No. 4,134,137 to Jacobs et al, issued Jan. 9, 1979—A single wire microelectrometer imaging system is disclosed which includes a means to measure dark decay. A photoreceptor can be selected to minimize dark decay due to a scanning process requiring a finite length of time. A multiple probe electrometer array is provided which comprises a number of single probe electrometers which increase the electronics and gap maintenance complexity while reducing mechanics, image interlace complexities, and processing time.

CROSS REFERENCE TO COPENDING APPLICATIONS

Copending patent application Ser. No. 08/585,133, now U.S. Pat. No. 5,703,487, filed in the name of S. Mishra on Jan. 11, 1996—A process is disclosed for ascertaining the microdefect levels of an electrophotographic imaging member comprising the steps of measuring either the differential increase in charge over and above the capacitive value or measuring reduction in voltage below the capacitive value of a known imaging member and of a virgin imaging member and comparing differential increase in charge over and above the capacitive value or the reduction in voltage below the capacitive value of the known imaging member and of the virgin imaging member. The entire disclosure of this application is incorporated herein by reference.

Copending patent application Ser. No. 08/960,673, entitled CONTACTLESS SYSTEM FOR DETECTING MICRODEFECTS ON ELECTROSTATOGRAPHIC MEMBERS, filed in the names of Z. Popovic et al. concurrently herewith—A contactless process is disclosed for detecting surface potential charge patterns in an electrophotographic imaging member including at least one photoconductive imaging layer having an imaging surface, providing a scanner including a capacitive probe having an outer shield electrode, maintaining the probe adjacent to and spaced from the imaging surface to form a parallel plate capacitor with a gas between the probe and the imaging surface, providing a probe amplifier optically coupled to the probe, establishing relative movement between the probe and the imaging surface, maintaining a substantially constant distance between the probe and the imaging surface, applying a constant voltage charge to the imaging surface prior to relative movement of the probe and the imaging surface past each other, the average surface potential of the imaging surface, measuring variations in surface potential with the probe, compensating the surface potential variations for variations in distance between the probe and the imaging surface, and comparing the compensated voltage values to a baseline voltage value to detect charge patterns in the electrophotographic imaging member. This process may be conducted with a contactless scanning system comprising a high resolution capacitive probe, a low spatial resolution electrostatic voltmeter coupled to a bias voltage amplifier, and an imaging member having an imaging surface capacitively coupled to and spaced from the probe and the voltmeter, the probe comprising an inner electrode surrounded by and insulated from a coaxial outer Faraday shield electrode, the inner electrode connected to an optocoupled amplifier, and the Faraday shield connected to the bias voltage amplifier. The entire disclosure of this application is incorporated herein by reference.

Copending patent application Ser. No. 08/961,436, entitled CONSTANT DISTANCE CONTACTLESS DEVICE, filed in the names of Z. Popovic et al. concurrently herewith—A contactless system is disclosed including an aerodynamically floatable device, a member having an outer surface adjacent to and spaced from the aerodynamically floatable device, a support mechanism adapted to support the aerodynamically floatable device for free movement toward and away from the outer surface of the member, the aerodynamically floatable device having a side adjacent to, spaced from, parallel to and facing the outer surface of the member, the aerodynamically floatable device also containing at least one passageway for directing at least one stream of a gas from the side of the aerodynamically floatable device toward the outer surface of the member with sufficient pressure to maintain the aerodynamically floatable device a constant distance from the outer surface of the member. This system may be utilized in a process comprising providing an aerodynamically floatable device spaced from an outer surface of a member, the aerodynamically floatable device being at least moveable toward and away from the outer surface of the member, the aerodynamically floatable device comprising at least one passageway for directing at least one stream of a gas from the moveable device toward the outer surface of the member, flowing a gas through the passageway with sufficient pressure to maintain the aerodynamically floatable device a constant distance from the outer surface of the member. The entire disclosure of this application is incorporated herein by reference.

BRIEF SUMMARY OF THE INVENTION

It is, therefore, an object of the present invention to provide improved processes and apparatus for detecting subtle surface potential charge patterns and thickness variations in an electrostatographic imaging member which overcomes the above-noted deficiencies.

It is still another object of the present invention to provide improved processes and apparatus for more accurately assessing detecting subtle surface potential charge patterns and thickness variations for an electrostatographic imaging member.

It is another object of the present invention to provide improved processes and apparatus for assessing detecting subtle surface potential charge patterns and thickness variations in electrostatographic imaging members without contacting the imaging surface of the imaging member.

It is yet another object of the present invention to provide improved processes and apparatus for rapidly assessing detecting subtle surface potential charge patterns and thickness variations in electrostatographic imaging members.

The foregoing objects and others are accomplished in accordance with this invention by providing a contactless process for detecting electrical patterns on the outer surface of a member comprising providing a member having a charge pattern on an outer surface, repetitively measuring the charge pattern on the outer surface of the member with an electrostatic voltmeter probe maintained at a substantially constant distance from the surface, the distance between the probe and the imaging member being slightly greater than the minimum distance at which Paschen breakdown will occur to form a parallel plate capacitor with a gas between the probe and the surface, the frequency of repetition being selected to cause all time dependent signals to fall out of phase by a predetermined amount, and averaging the out of phase time dependent signals over a sufficient number of measuring repetitions to eliminate the time dependent signals.

In one embodiment, the contactless process for detecting surface potential charge patterns in an electrostatographic imaging member comprises providing a cylindrical electrostatographic imaging member having an outer imaging surface and an imaginary axis, providing an electrostatic voltmeter probe having a charge measuring end spaced from the outer imaging surface, maintaining the distance between the charge measuring end of the probe and the imaging surface substantially constant, the distance between the charge measuring end and the imaging member being slightly greater than the minimum distance at which Paschen breakdown will occur to form a parallel plate capacitor with a gas between the probe and the imaging surface, establishing relative movement between the probe and the imaging surface, depositing a charge on the imaging surface along a narrow predetermined path immediately prior to relative movement of the probe over the charge on the imaging surface, the deposited charge having a surface potential pattern containing low resolution variations having of a width of between about 0.1 millimeter and about 5 millimeters, repetitively measuring the deposited charge on the imaging with the electrostatic voltmeter probe, the frequency of repetition being selected to cause all time dependent signals to fall out of phase by a predetermined amount, and averaging the out of phase time dependent signals over a sufficient number of measuring repetitions to eliminate the time dependent signals to detect the low resolution variations in the surface potential charge pattern.

The contactless scanning system of this invention may comprise a device to support and rotate a cylindrically shaped electrostatographic member having an imaging surface, a charging device adapted to deposit a charge on the imaging surface along a predetermined narrow path, an electrostatic voltmeter probe adjacent to and spaced from the imaging surface to form a parallel plate capacitor with the surface, a device adapted to position the charging device and the probe on the narrow path, the charging device comprising a central pin electrode and a concentric shield electrode, the central pin electrode having an axis positioned substantially perpendicular to the imaging surface.

DETAILED DESCRIPTION OF THE DRAWING

Figure 1:
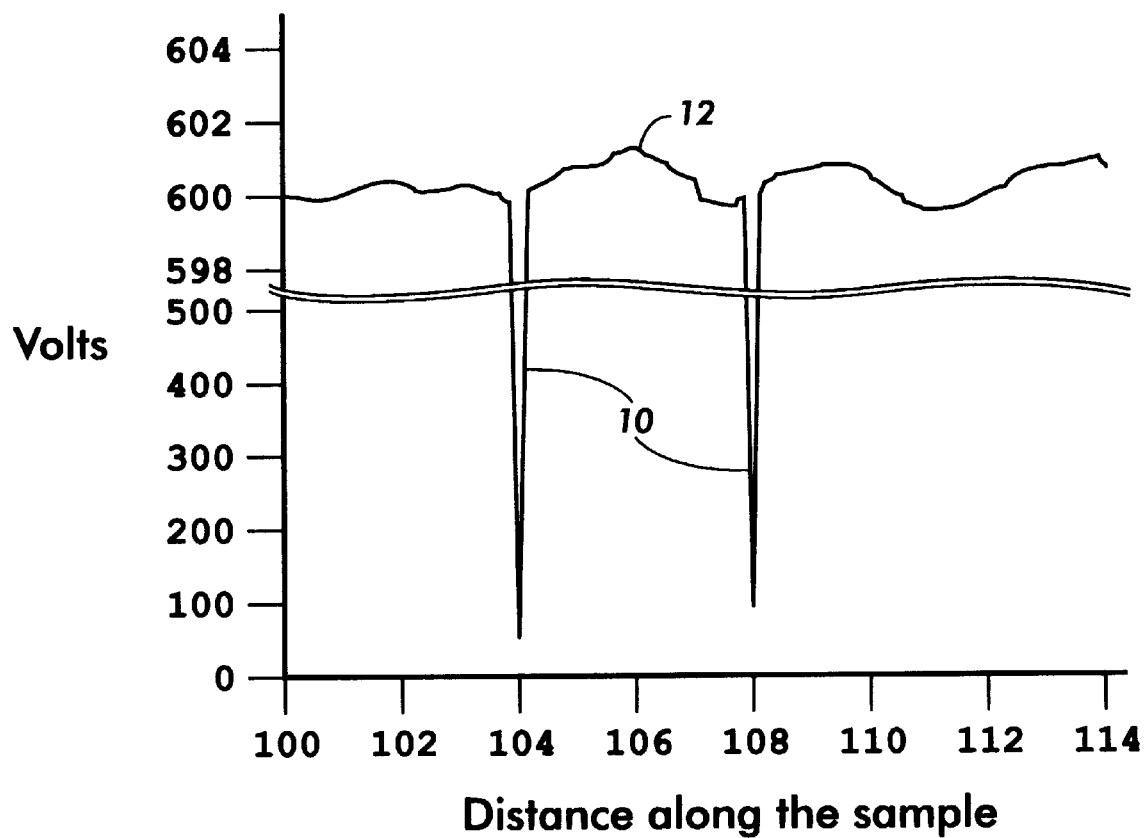
FIG. 1 is a graph illustrating voltage variations which can occur on a charged imaging surface of a photoreceptor.

FIG. 1 illustrates voltage variations which can occur on a charged imaging surface of a photoreceptor. These voltage variations include, for example, charge deficient spots (CDS's) where the voltage sharply drops hundreds of volts along an extremely short lateral distance along the imaging surface of about 10 micrometers to about 100 micrometers. Typical two dimensional lateral sizes of charge deficient spots are on the order of between about 10 micrometers×10 micrometers and about 100 micrometers×100 micrometers. Line graph voltage profiles of such a charge deficient spot has the appearance of long narrow spikes 10 extending downwardly from the generally horizontal surface charge profile 12. These are classified as micro-defects. Any probe for detecting a charge deficient spot must detect voltage changes over an extremely small horizontal surface area. The shield of the probe for detecting a charge deficient spot must be biased at about the average voltage of the photoreceptor surface (average of the generally horizontal surface charge profile 12) to avoid air breakdown and destructive arcing between the probe and the surface of the photoreceptor. Thus, a shield voltage which is within about 300 volts of the voltage on the photoreceptor surface will prevent arcing. Thus, for measuring charge deficient spots, it is not necessary to have a very precise measurement of the average voltage of the photoreceptor surface (background voltage) because the main function of background voltage is to bias the shield of a charge deficient measuring probe to prevent arcing. The resolution of a charge deficient spot probe depends on the size of the probe electrode and the distance between the probe and the photoreceptor surface, typically very close to the photoreceptor, e.g. 100 micrometers Another type of voltage variation encountered on a photoreceptor is one which gradually fluctuates between about 1 to about 2 volts over a lateral distance along the imaging surface of between about 1 to 2 millimeters. For illustration in one dimension, a line graph voltage profile of such voltage variation appears as a rippled, substantially horizontal surface charge profile 12 (baseline voltage curve) as shown in FIG. 1. These are termed as macro-nonuniformities. The absolute measurement of extremely subtle voltage variation defect is particularly difficult to rapidly detect and cannot be detected by scanners designed for detecting charge deficient spots. The gradual voltage fluctuation nonuniformity in the substantially horizontal surface charge profile 12 is especially critical for advanced, highly sophisticated superimposed multiple image systems, particularly color imaging systems where at least one toner image is formed over at least one previously formed image and the resulting plurality of developed images are simultaneously transferred to a receiving member to produce full color prints or copies. As explained above, the charging uniformity requirements for superimposed colored image systems is on the order of less than 5 volts. In other words, for testing of photoreceptors to be used in high tolerance imaging systems such as superimposed colored image systems, the electronic map of the charged surface of the photoreceptor should be accurate within 1 to 2 volts with a lateral resolution of less than about 1 millimeter. If the charging uniformity of a photoreceptor production batch fails to meet these stringent tolerance requirements, color shifting can occur during imaging which leads to copy quality degradation.

Unlike a scanner for charge deficient spots, the scanner system of this invention detects very small changes, e.g. about 1 to 2 volts over a relatively large area, e.g. about 1 mm×1 mm. The electrostatic voltmeter probe for detecting macro non-uniformities is far more sensitive and gives an absolute measurement of voltages, but at the cost of resolution. For improving the resolution the probe is brought as close to the photoreceptor as possible, but more than the limit at which arcing begins to take place. This distance is typically about 100 micrometers to about 500 micrometers. The resolution of the probe for detecting low total voltage at closer distances is about 1 millimeter. Since the sensitivity of measurements (i.e. measuring small voltage changes) is very important in the scanner system of this invention, time dependent high frequency noise should be reduced to the maximum without affecting the macro-uniformity signals. One noise reduction technique involves phase stepped noise reduction which is discussed in detail hereinafter.

Figure 2:
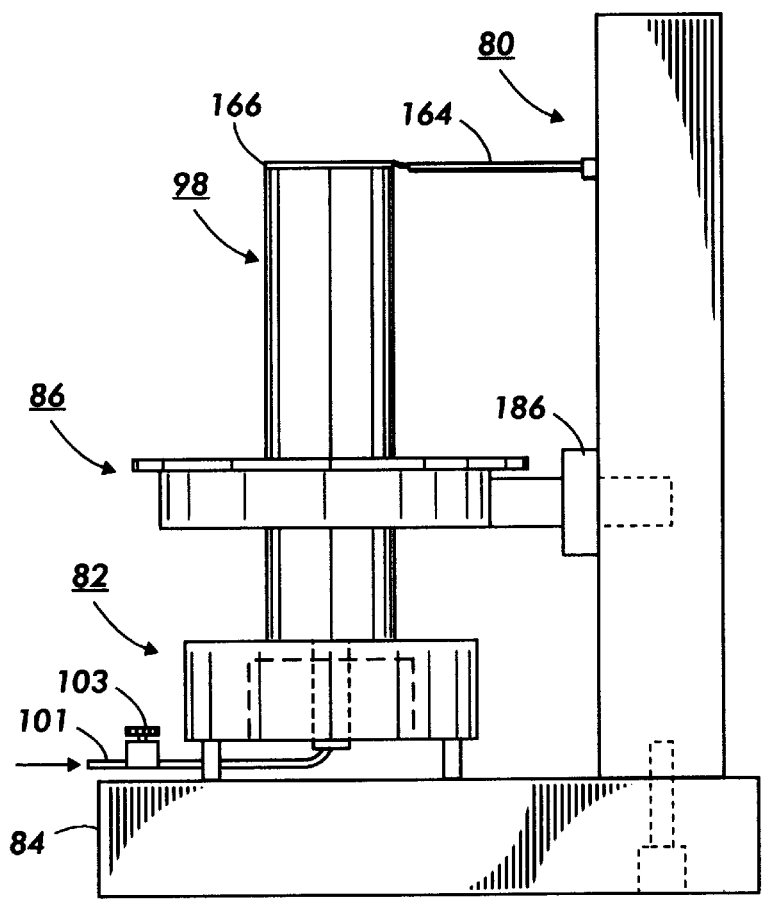
FIG. 2 is a schematic side view in elevation of a scanner system of this invention.
Figure 3:
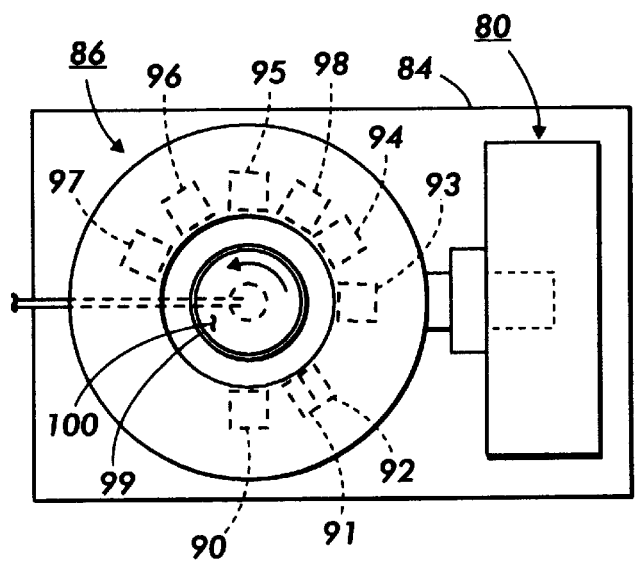
FIG. 3 is a schematic plan view of the scanner system illustrated in FIG. 2.

In FIGS. 2 and 3, one example of a preferred scanning system of this invention is illustrated comprising a vertical translation stage 80. Any suitable vertical translation stage may be utilized such as a ball and screw (not shown) vertical translation stage (e.g. Model ATS500045 available from Aerotech) in which the screw extends from the bottom of the vertical translation stage 80 to the top to support and reciprocate the ball as well as annular platform ring 86 which is attached to the ball. Vertical translation stage Model ATS500045 has a specification of 4.5 micrometers straightness and flatness of 6 micrometers deviation for 18 inches of travel. Other typical devices for reciprocating the annular platform ring 86 include, for example, drive belts, air cylinders, linear motors, rack and pinion system, and the like. Preferably, mounting plate 186 of vertical stage 80, to which the ring 86 is attached, extends over a large area, such as, for example, an area of 10 inch×10 inch (25.4 cm×25.4 cm) to enhance stability of motion quality. The base 84 of translation stage is large in area of 3 feet×3 feet and is made of material such as marble to provide stability. Alternatively, translation stage 80 may be fastened directly to any other suitable stable structure such as a table or floor (not shown).

A rotary stage 82 is mounted to base 84 which also supports vertical translation stage 80. A typical rotary stage is Model ADR 200-5, available from Aerotech having a specification of 4 micrometer wobble at 18 inches (46 cm) along an imaginary extension of the axis of the rotary stage. Any other suitable rotary stage 82 substantially free of wobble may be used. Rotary stage may be driven by any suitable drive device such as a direct drive servo, a pillow block and motor system, a spindle mount, direct drive motor, and the like. A conventional encoder is preferably included in the drive for the rotary stage.

As described above annular platform ring 86 is supported and moved by the vertical translation stage 80. A typical arrangement of test components on and supported by ring 86 are a charging device 90 for depositing an electrostatic charge (e.g. corotron or scorotron), an electrostatic voltmeter probe 91 to determine average potential of the imaging surface after charging, a high resolution scanning probe 92 for scanning the charged imaging surface, exposure device 93 such as a light emitting diode for discharging the imaging surface, an electrostatic voltmeter 94 for measuring potential on the photoreceptor after discharge, erase exposure light 95 such as a light emitting diode for erasing the imaging surface, an electrostatic voltmeter 96 to measure residual potential after erase, and optional thickness gage 97. Generally, the order of placement of the test components on ring 86 is single pin central electrode charging device 90 first followed by an electrostatic voltmeter probe 91, high resolution scanning probe 92, exposure device 93, electrostatic voltmeter 94, erase exposure light 95 and an electrostatic voltmeter 96. The optional thickness gauge 97 can be placed anywhere along the ring 86 but typically after erase exposure light 95. The relative angular distances between the test components mounted on the ring 86 is dependent on the experiment of interest and machine configuration for which the photoreceptor element is being tested. All the distances are measured from the single pin central electrode charging device 90. A typical angular distances for the high resolution scanning probe 92 measuring the voltage level on the photoreceptor before exposure, for example, lies between about 10 degrees and about 100 degrees. The companion electrostatic voltmeter 91 is placed adjacent to and just before the high-resolution probe. All the elements 91 through 95 are aligned with the peak of the charging profile of the charging device 90. The charging profile is almost gaussian and is described in greater detail hereinafter. The angular distance of the electrostatic voltmeter 94 to measure the image potential is between about 20 degrees and about 180 degrees. The exposure device 93 is placed between the electrostatic voltmeter 94 single pin central electrode charging device 90. The device 94 is placed right adjacent to the exposure light 93. Typical angles for the electrostatic voltmeter 94 are between about 25 degree about 185 degrees. The erase exposure light 95 is placed after the electrostatic voltmeter 94 and the electrostatic voltmeter 96 is placed right after the erase exposure light 95. The electrostatic voltmeter 96 is to record the residual voltage. The optional thickness gauge 96 can be placed anywhere around the ring 86, and typically, after the electrostatic voltmeter 94 for measuring the image potential or electrostatic voltmeter 96 for measuring the residual potential after erase. This describes a typical arrangement. However, sometimes one may be interested in studying the effect of exposure light on micro-defects. In this case a high-resolution probe 98 may be mounted after the electrostatic voltmeter 94 just as devices 91 and 92. On other occasions, one may be interested in studying effect of longer dark decay period on the macro and micro uniformity of the imaging member. In this case, the exposure may be switched off and macro uniformity recorded on the electrostatic device 94 and micro uniformity (defects) on a high resolution probe 98, if employed.

Figure 4:
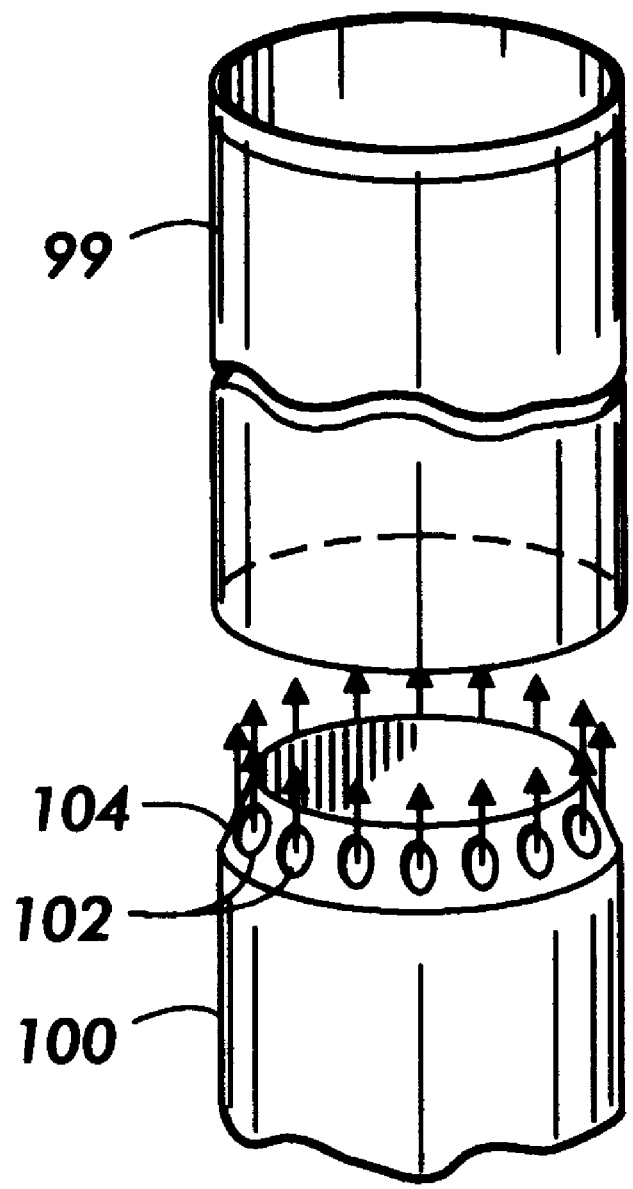
FIG. 4 is a schematic sectional view of a photoreceptor belt being mounted on a supporting mandrel.

Rotary stage 82 supports and rotates a cylindrical member 98. Cylindrical member 98 comprises flexible photoreceptor belt 99 to be assessed supported on mandrel 100 (see FIG. 4). Cylindrical member 98 may alternatively comprise, for example, a coated drum photoreceptor or an electrostatographic belt member such as a flexible intermediate transfer belt supported on a rigid drum mandrel 100. It is preferred that mandrel 100 be mounted on the turntable of rotary stage 82 to support either flexible belt 99 or a hollow electrostatographic drum. The ring 86 is generally coaxial aligned with cylindrical member 98. Ring 86 is transported by the translation stage 80 in a direction parallel to the surface of the photoreceptor belt 99 to traverse the photoreceptor from one end to the other. The spacing or gap distances of charging device 90 and various electrostatic measurement probes such as 92 from the outer surface of photoreceptor 99 is typically maintained within about 7 micrometers during the entire scan of, for example, a three pitch photoreceptor belt supported on cylindrical mandrel 100. The gap distance setting for the charging device 90 from the photoreceptor ranges from about 0.25 millimeter to about 5 millimeters. This gap is from the grid to photoreceptor for scorotrons and from the shield to photoreceptor for corotron devices. Preferably, the axis of mandrel 100 is aligned vertically so ring 86 traverses mandrel 100 from one end to the other in a vertical direction. Any suitable mandrel 100 may be utilized. For flexible belts, mandrel 100 is connected to a source of compressed fluid, such as air, through feed line 101 (see FIG. 2). When utilizing a mandrel 100 in combination with a source of compressed fluid to expand the flexible belt 99, (see FIG. 4) the drive shaft (not shown) for the turntable of rotary stage 84 may be hollow and connected to mandrel 100 at one end and at the other end to the feed line 101 through a conventional rotary union (not shown) to allow feeding of compressed air from any suitable outside source (not shown). Air introduced from the feed line 101 into the interior of mandrel 100 escapes out of air exhaust holes 102 located in the chamfered edge 104 of the upper end of the mandrel 100. When a flexible belt 99 is placed over the upper end of mandrel 100, the escaping air expands belt 99 thereby facilitating sliding of the belt downwardly on a thin air bearing onto mandrel 100. Any suitable valve 103 (see FIG. 2) may be used to initiate or terminate supply of air to mandrel 100 through feed line 101. Termination of air flow after the belt 99 is slid onto the mandrel 100 allows the belt 99 to shrink and cling snugly onto mandrel 100 without any visible wrinkles or bubbles. The mounting of a belt onto a drum with the aid of air is known and described in for example, in U.S. Pat. Nos. 5,415,961 and 5,518,854, the entire disclosures thereof being incorporated herein by reference. If desired, the mandrel 100 for a flexible belt may comprise a rigid cylinder or a hollow cylinder with thick walls and a slot (not shown) extending axially from one end of the drum to other. The slot may have tapered cross-section to receive a wedge. When a photoreceptor belt is slid onto the mandrel, the wedge is used to press the flexible belt (preferably along the belt seam) into the slot. Thus, the wedge tightens the belt onto the mandrel. The wedge may be retained in the slot by any suitable device such as, for example, screws, latches, magnets, levers and the like. For rigid photoreceptor drums, the mandrel for supporting the drum on the rotary stage may comprise any suitable device such as an inflatable or otherwise expandable mandrel which is expanded after an electrostatographic imaging drum is slid over the mandrel prior to mandrel expansion. Instead of an inflatable mandrel, one may use other devices such as a compressible donut which diametrically expands when it is flattened by axially applied pressure. If the drum is magnetically attractable, permanent or electromagnets may be employed to secure the drum to the rotary stage. If desired, a rigid photoreceptor drum may be mounted between two cone shaped mounting pieces aligned axially with the apex of each cone pointing toward each other. One of the cones may be secured to the rotary stage. The distance between the two mounting pieces can be initially increased to allow placement of the cylindrical test sample between the mounting pieces and the distance between the cones may thereafter be reduced by any suitable device, such as a threaded bolt extending axially through the upper cone into a threaded axially aligned hole in the lower cone, to clamp and secure the test sample in place on the rotary stage.

Annular platform ring 86 surrounds and is concentric with cylindrical member 98. Movement of the annular platform ring 86 along the surface of cylindrical member 98 may be continuous or incremental. When movement of ring 86 is continuous during scanning of the rotating cylindrical member 98, the scanning path traces a helical path along the surface of the cylindrical member 98 similar in appearance to the threads on a machine screw. In incremental scanning, ring 86 moves in increments along the surface of the cylindrical member 98 and readings are taken while the ring 86 is stationary and cylindrical member 98 is revolving. A slight overlap of the path (if helical) or paths (if circular) scanned is desirable to ensure complete mapping of the imaging surface of an electrostatographic imaging member. Scanning of the cylindrical member 98 by the probe 92 on the ring 86 may occur during only one direction of movement of the ring over the surface of the drum or in both directions. Generally, the rotary stage 82 remains in motion during scanning. Any suitable rotational speed may be utilized. A typical rotation speed is 100 revolutions per minute. However, any other suitable speed may be employed as long as the scanning objectives are met.

Figure 5:
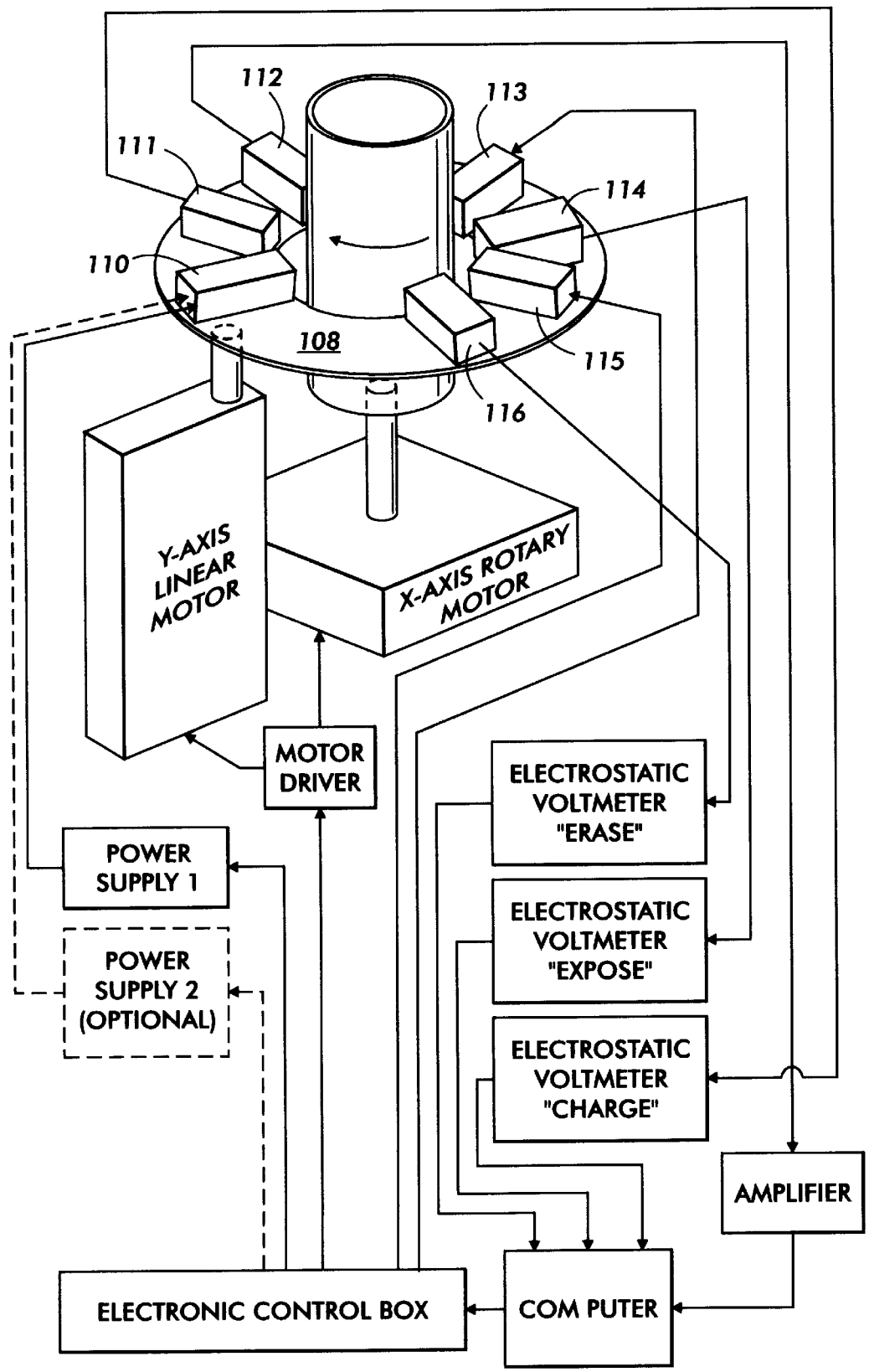
FIG. 5 is a schematic diagram showing the connections of the various components and instruments for measuring voltage profile.

A schematic diagram showing the connections of the various components and instruments associated with some of the devices shown in FIGS. 2 and 3 for measuring voltage profile is illustrated in FIG. 5. As an alternative process to that illustrated in FIGS. 2 and 3, the drum shown in FIG. 5 is rotated in the opposite direction. The X-axis rotary motor for rotating the drum includes a conventional encoder. Thus, the components on the ring illustrated in FIG. 5 are in an essentially mirror image arrangement of that illustrated in FIGS. 2 and 3. More specifically, a typical arrangement of test components on and supported by ring 108 are a charging device 110 (corresponds to 90 in FIG. 3) for depositing an electrostatic charge (e.g. corotron or scorotron), an electrostatic voltmeter probe 111 (corresponds to 91 in FIG. 3) to determine average potential of the imaging surface after charging, a high resolution scanning probe 112 (corresponds to 92 in FIG. 3) for scanning the charged imaging surface, exposure device 113 (corresponds to 93 in FIG. 3) such as a light emitting diode for discharging the imaging surface, an electrostatic voltmeter 114 (corresponds to 94 in FIG. 3) for measuring potential on the photoreceptor after discharge, erase exposure light 115 (corresponds to 95 in FIG. 3) such as a light emitting diode for erasing the imaging surface, and an electrostatic voltmeter 116 (corresponds to 96 in FIG. 3) to measure residual potential after erase.

During scanning, it is desirable to reduce electronic noise. One method for noise removal involves oversampling data and averaging across an entire wavelength of the noise frequency along the direction in which measurements are being made. This technique eliminates noise at many harmonics of the original frequency at the same time. However, it limits the resolution of a measurement. For example, in a uniformity scanner with a 21 cm diameter drum rotating at a speed of 100 RPM, removal of noise at 60 Hz gives a resolution limit of 18 mm. At a drum rotational speed of 100 RPM, this is the equivalent surface distance of a single 60 Hz wave. The slowing down of the measurement presents a problem because it would then require a week to run a single test. Other techniques for reduction includes filters. Both analog and digital filters can be used. However, with xerographic measurements, the presence of several widely different noise frequencies renders the calculation of digital filter coefficients a very tedious exercise. With analog filters such as notch filters interference of one with the other is a problem. Since electrostatic probes are the greatest generator of noise and since probe noise frequency varies from probe to probe and also changes with environment and usage, hard wired notch filters require continuous tuning. Yet another technique utilizes the FFT (Fast Fourier Transform). These frequency domain manipulations (FFT) will remove 60 Hz and harmonics of "real" variations on the photoreceptor along with the line noise. However FFT can be computationally complex.

When performing a continuous one-dimensional measurement (time domain) of a two dimensional (generally spatial domain) quantity, one can arrange the measurement parameters such that the phase stepping of any particular frequency across one of the spatial dimensions allows averaging to virtually eliminate a frequency component which is time-domain based. Mapping of a photoreceptor for a particular voltage on a rotating drum is done by a single measurement probe which moves continuously in a direction perpendicular to drum rotation. Continuous measurement is possible since the response time of the measurement is fast. Continuous measurements are preferred because the charging potential is easily controlled. Alternately, a stepped measurement could be done if the response time of the probe is slow and where uniformity of voltage is not the objective. For example, in thickness measurement the stepped measurements are preferred. This is done for uniformity mapping, the data is continuously acquired along a helical path to span the full surface. Along this path charging and measurement takes place. Data are acquired continuously in time, yet the final result will be a two-dimensional spatial map. An X-Y map is generated by plotting data obtained in each revolution along the X axis while stepping along the y axis each successive revolution by the distance through which the probe moves in a vertical direction after each revolution of the drum. This facilitates noise reduction for a particular frequency and many harmonics with simple averaging. This method is especially useful with very large data sets where complex mathematical methods of noise reduction require too much computer processing power and time.

Figure 6:
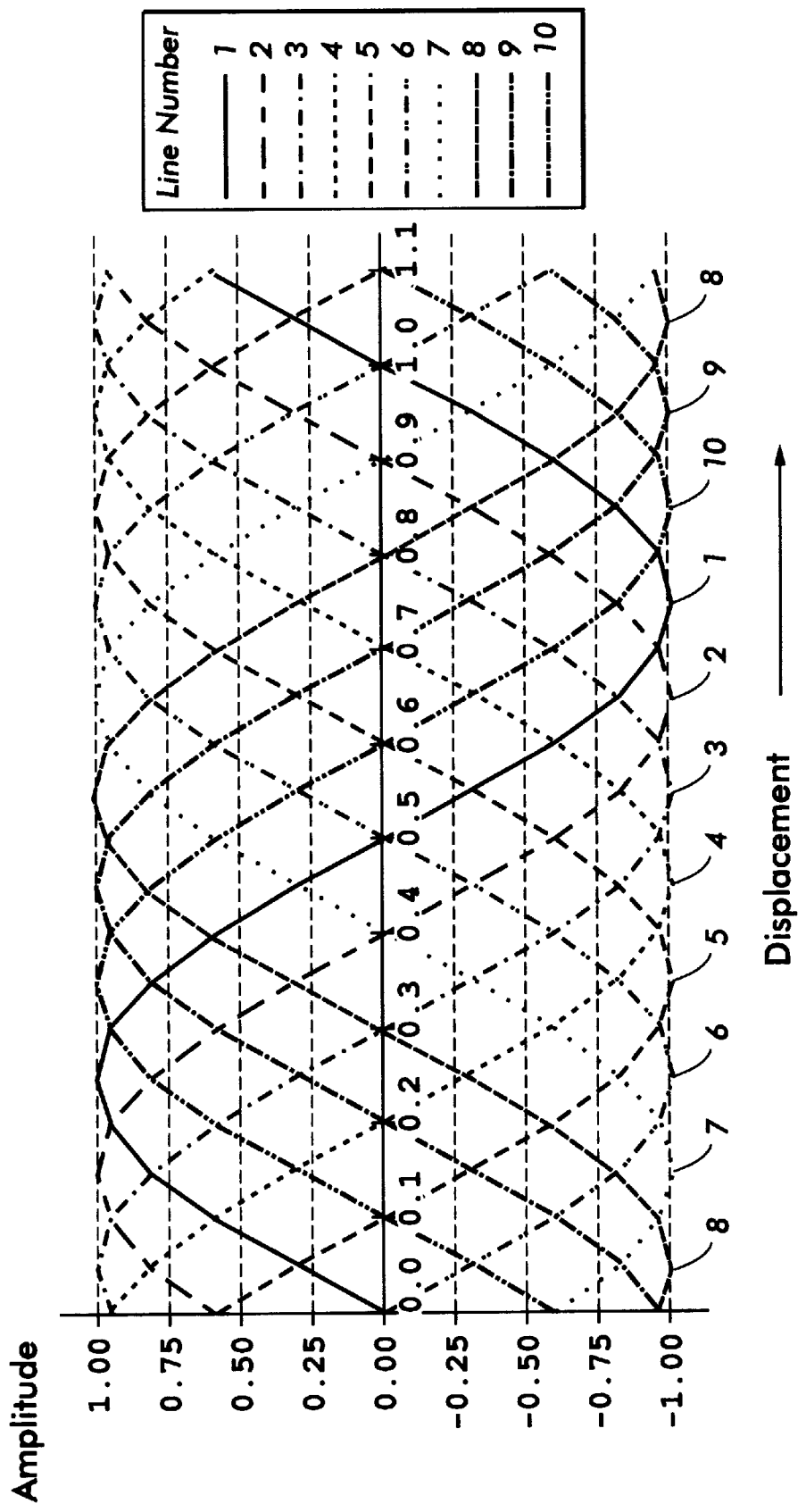
FIG. 6 is a schematic depiction of phase stepped noise reduction in which the rotational speed of a drum is selected in such a way that the wave corresponding to a noise frequency occurring continuously in time is advanced by a fraction of wavelength in the next revolution.

For example, to obtain a vertical resolution of 1 millimeter, 10 series of measurements are made within 1 vertical millimeter. The rotational speed of the drum is selected in such a way that the wave corresponding to a noise frequency occurring continuously in time is advanced by a fraction of a wavelength in the next revolution. FIG. 6 illustrates an example of phase stepping. The values along the vertical axis represent the noise component of a measurement and the values along the horizontal axis represent displacement along the circumference of the drum. Points in FIG. 6 are acquired with 10 times oversampling for the desired resolution in the "Y" direction, parallel to the axis of drum rotation. This means that a speed of drum rotation is selected to ensure that the frequency chosen for elimination is stepped by $1/10^{th}$ of a wavelength in phase with each drum rotation. Thus, in this example, each successive line has the frequency chosen for elimination $1/10^{th}$ of a wavelength out of phase from that of the preceding line. Averaging in the "Y" direction gives a very large reduction in the noise frequency. This method has shown a better than 20:1 noise reduction on noise frequencies while still showing real photoreceptor features at those frequencies. Averaging of the values of all the noise curves shown in FIG. 6 along any vertical line gives zero. Thus, when the summation is taken over the "Y" direction, a noise frequency that is phase stepped properly is effectively suppressed. This basic concept is referred to hereinafter as Phase Stepped Noise Reduction.

Phase Stepped Noise Reduction also equally suppresses the harmonics of a noise frequency.

If several noise frequencies are present, then one can obtain an optimum value of rotational speed at which all present noise frequencies will be suppressed.

Additionally, Phase Stepped Noise Reduction is a selective filter. Only frequencies that remain constant in time will have this phase relationship across many scan lines and will be averaged out. Any variation of the same frequency, which vary spatially across the "X" direction and are in phase (as one would expect from any material to be measured) will not be removed by Phase Stepped Noise Reduction. In this type of measurement, the only truly constant frequencies in the time domain are noise frequencies.

In the uniformity scanner of this invention, some additional suppression is also obtained in the "X" direction (along the circumference of the drum due to averaging along this direction. More specifically, processing software is used to average 10 points in the "X" direction as well as 10 points in the "Y" direction for Phase Stepped Noise Reduction, so each output data point is actually the average of 100 points that were averaged together.

A description of the algorithm used to determine the proper rotational speed and sample size for averaging follows.

Figure 7:
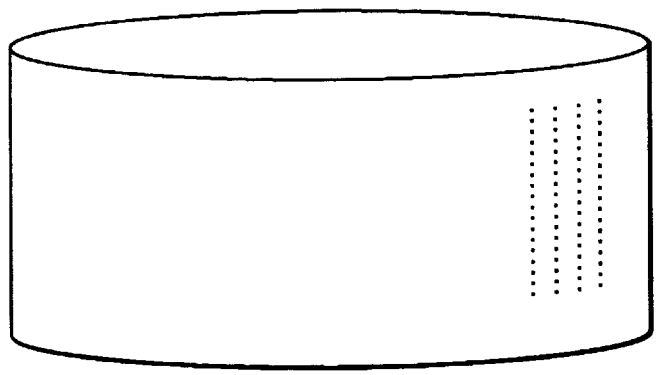
FIG. 7 is a schematic illustration of sampling points at which measurements are taken on an imaging belt mounted on a drum.

When using the an encoder to trigger sampling, the sampling points at which measurements are taken on the imaging belt mounted on a drum are aligned vertically with their corresponding sample points in subsequent revolutions of the drum as illustrated in FIG. 7. This vertical alignment of sample points permits oversampling in the vertical direction followed by averaging of the vertically aligned sample points.

Encoder triggered sampling also has the effect of translating time based frequencies into spatial frequencies, assuming a constant rotational speed of the drum. When the rotational speed of the drum holding the imaging belt sample does not allow for an integer number of noise cycles during one revolution of the drum, the next vertically aligned sample point will include the noise, but with a phase shift. When enough points along a vertical line have been accumulated to include an integer number (greater than one) of noise cycles, with no fractional portion of a noise cycle left-over, an average of these measurements yields the average of the actual desired quantity without the noise component. Including samples along an integer number of complete noise cycles causes the noise components to cancel one another.

Figure 8:
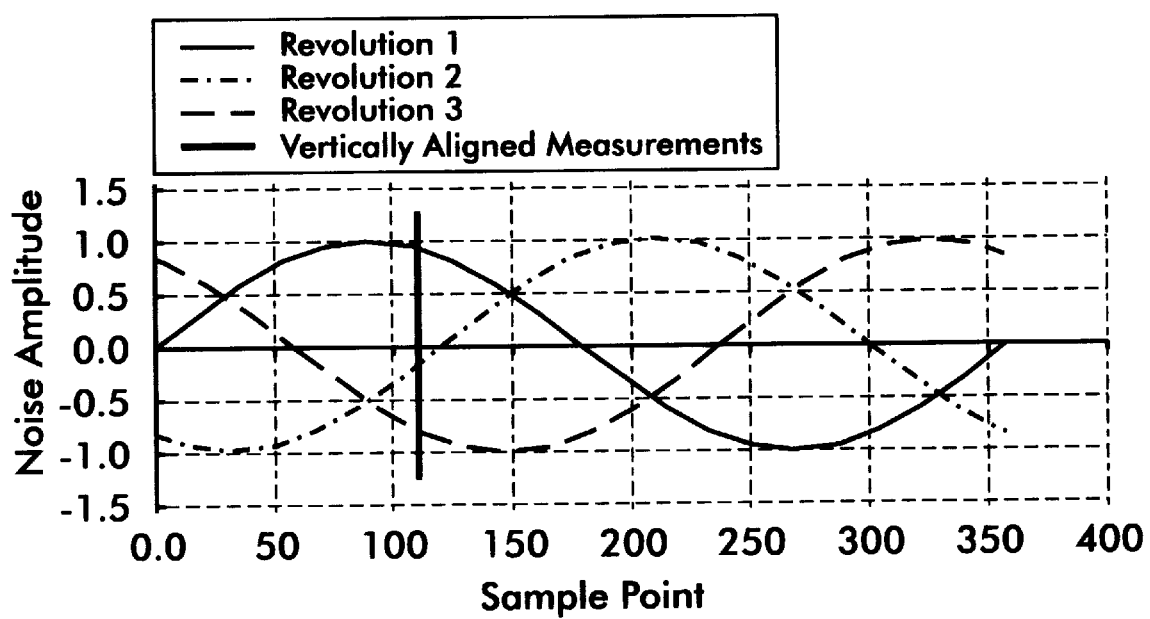
FIG. 8 is a schematic illustration of the portions of noise that are measured in consecutive vertical samples when the noise cycle is shifted in phase.

Depicted in FIG. 8, are the portions of noise that would be measured in consecutive vertical samples when the noise cycle is shifted in phase by one full cycle per three revolutions. It can be seen that an average of these three points would eliminate the noise component. In FIG. 8 the values along the vertical y axis represent the noise signal levels and the values along the horizontal x axis represent the spatial displacement. The algorithm for determining the number of vertical samples that are included in this average to exactly eliminate a certain noise frequency at a certain rotational speed is described as follows in conjunction with the Flow Diagram illustrated in FIG. 9.

Predetermined parameters (R and Ni), and variables ($L_i$, $C_i$, $P_i$, $S_i$, and Q) for solving for the parameters, used for determination of the number of samples that should be averaged to eliminate noise are listed as follows:

R=Rotational Speed $N_i$=Noise Frequency $L_i$=Number of Noise Cycles per revolution—exact $C_i$=Number of Complete Noise Cycles Per Revolution $P_i$=Fraction of Noise Cycle that is remaining (not complete).

$S_i$=Number of Revolutions that must be averaged to eliminate the Noise Frequency, $N_i$ Q=Number of Revolutions that must be averaged to eliminate all Noise Frequencies The subscript "i" for the above parameters represent integers wherein $N_1$ is noise frequency 1, $N_2$ is noise frequency 2, etc.; $L_1$ is the number of noise cycles per revolution for noise frequency 1 at rotational speed R, $L_2$ is the number of noise cycles per revolution for noise frequency 2 at rotational speed R. etc.; $C_1$ is the number of complete noise cycles per revolution for noise frequency 1 ($N_1$); $C_2$ is the number of complete noise cycles per revolution for noise frequency 2 ($N_2$), etc.; $P_1$ is the fraction of noise cycle that is not complete (or remaining) per revolution for noise frequency 1 ($N_1$); $P_2$ is the fraction of noise cycle that is not complete (or remaining) per revolution for noise frequency 2 ($N_2$), etc.; Si is the number of revolutions that must be averaged to eliminate the noise frequency 1, ($N_1$); and $S_2$ is the number of revolutions that must be averaged to eliminate the noise frequency 2 ($N_2$), etc. Units that may be used for these parameters and variables are as follows:

R=rotations per minute

N=Hz

L=cycles per revolution

C=cycles per revolution

P=cycles per revolution

S=no units

Q=no units

Figure 9:
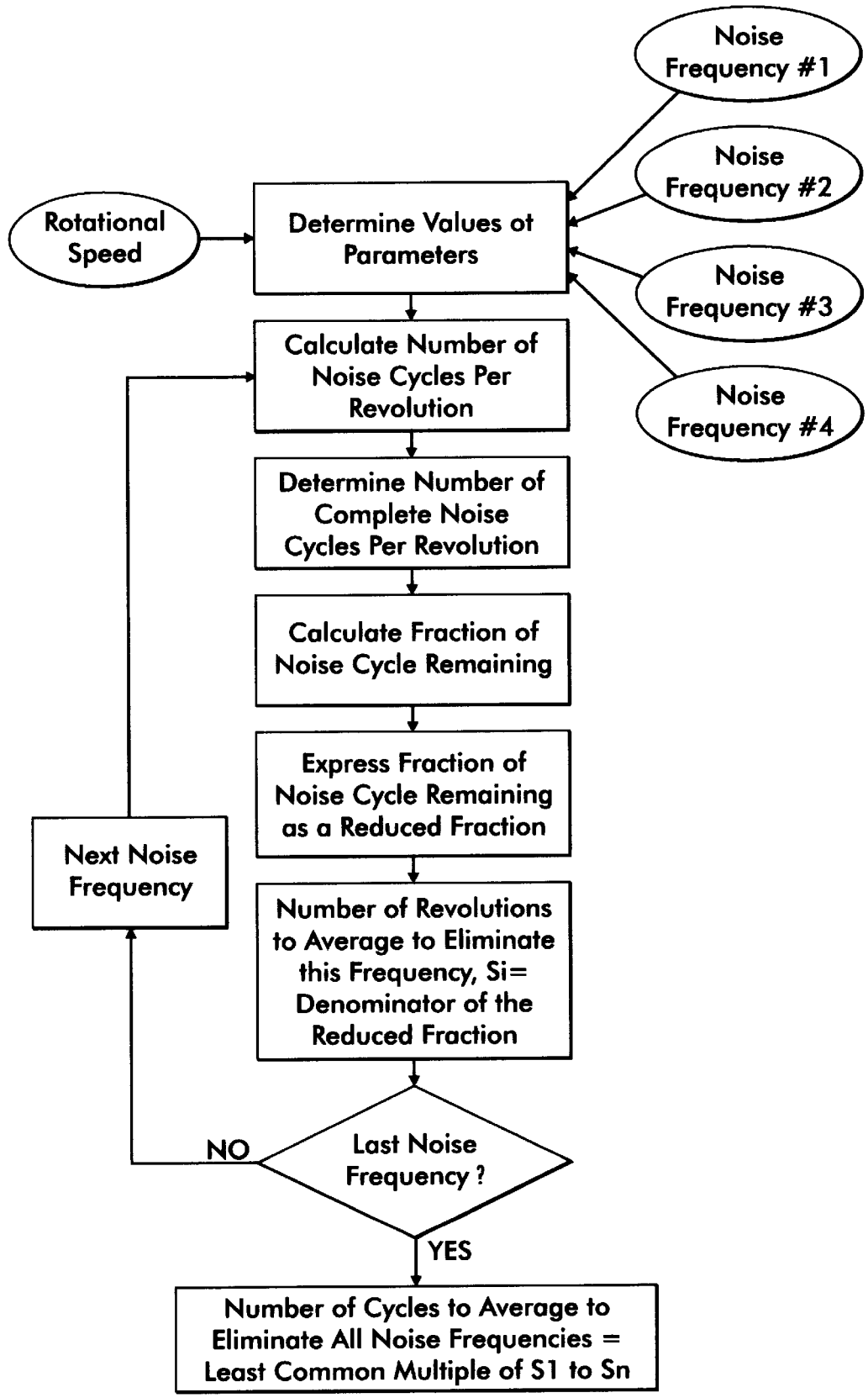
FIG. 9 is a Flow Diagram for determining the number of vertical samples that are included in calculations to eliminate a certain noise frequency at a certain rotational speed.

Thus, referring to flow diagram illustrated in FIG. 9, the input including parameters R and N is represented by the first box in the flow diagram.

The number of noise cycles per revolution (L) is equal to the noise frequency divided by the rotational frequency:

$L=[(60 \text{ s/minute})N_i]/R$

This calculation is represented by the second box in the flow diagram.

The number of complete noise cycles per revolution (C) is the integer nearest to the number of noise cycles per revolution that is not greater than the number of noise cycles per revolution. This determination is represented by the third box in the flow diagram.

The left-over or remaining fraction of a noise cycle (P) remaining is equal to the number of noise cycles per revolution minus the number of complete noise cycles per revolution.

$P_i=L_i-C_i$

This calculation is represented by the fourth box in the flow diagram.

The fractional amount of the noise cycle that is incomplete, $P_i$, should be expressed as a reduced fraction:

$P_i=\text{numerator}_i/\text{denominator}_i$

This determination is represented by the fifth box in the flow diagram.

S, the number of revolutions that must be averaged in order to eliminate the noise frequency, $N_i$, will be equal to the denominator of the fractional amount of the noise cycle that is incomplete:

$S_i=\text{denominator}_i$

This determination is represented by the sixth box in the flow diagram.

The number of revolutions that should be included in the averaging to eliminate all targeted noise frequencies (Q) will be the least common multiple of the numbers of revolutions that must be averaged in order to eliminate each of the individual noise frequencies:

Q=Least Common Multiple of $S_i$, $S_2$, $S_3$ . . .

This calculation is represented by the eighth box in the flow diagram.

Example I below illustrates an application of the above described technique.

Figure 10:
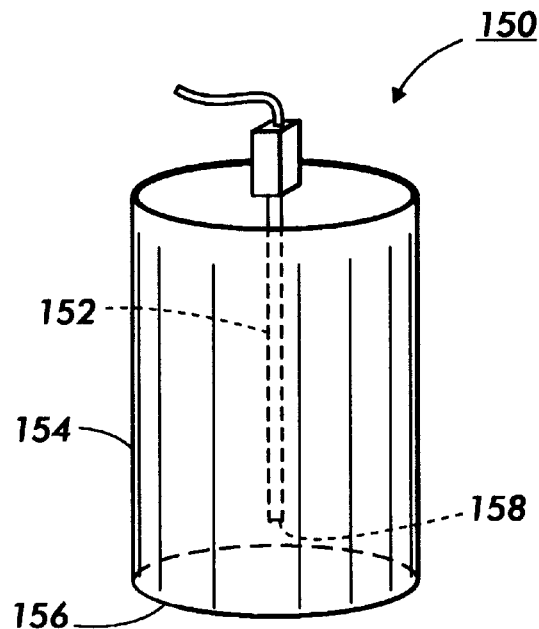
FIG. 10 is a schematic sectional view of a corotron charging device used in the scanner system of this invention.

A preferred charging device used for the uniformity scanner is discussed below. Although other devices such as a truncated scorotron or a corotron could be used for certain specific situations. With reference to FIG. 10, a corotron 150 for the scanning system of this invention is shown comprising a single pin central electrode 152 surrounded by a concentric shield electrode 154. Preferably, the central electrode 152 of the corotron 150 has a diameter between about 10 micrometers and about 200 micrometers. A typical diameter for the central electrode 152 is about 100 micrometers. Generally, the distance between the outer surface of the central electrode 152 and the inner surface of the conductive shield electrode 154 is between about 0.5 centimeter and about 1 centimeter. A typical distance between the bottom 156 of the shield 154 and the outer surface of the electrostatographic imaging member is about 1 millimeter. The distance from the charging end 158 of a central pin electrode 152 and the imaging surface of the photoreceptor (not shown) is typically between about 2 millimeters and about 5 millimeters. The central electrode and shield material comprise any suitable electrically conductive material. Typical electrically conductive materials include, for example, titanium, platinum, gold, tungsten, stainless steel, gold coated, other high melting point non corrosive metals, and the like. Preferably, these electrically conductive materials are stable under operating conditions and resistant to corrosion in air at high applied voltages. Sufficient voltage is applied to the central electrode to achieve air breakdown. Generally, the high voltage applied to the central pin electrode 152 during charging is between about 2 kilovolts and about 10 kilovolts. The shield 154 may be of any suitable thickness. Typical shield thicknesses are between about 100 micrometers and about 2 millimeters. The thickness is preferably sufficient to allow the shield to retain its shape while unsupported. Preferably, the outside diameter for the shield 154 is between about 1 centimeter and about 2 centimeters. With traditional charging corotrons, the entire width of a photoreceptor is charged as the photoreceptor is subjected to charging, scanning, discharge and, optionally, other treatment cycles. Since many of these treatment cycles are necessary when using a narrow scanning probe to electronically map the large surface of a photoreceptor, excessive fatiguing of a photoreceptor can occur by the time scanning of the entire surface of the photoreceptor is completed. The restricted area charged by the charging device of this invention prevents excessive fatiguing of the photoreceptor encountered with traditional full width charging corotrons.

Figure 11:
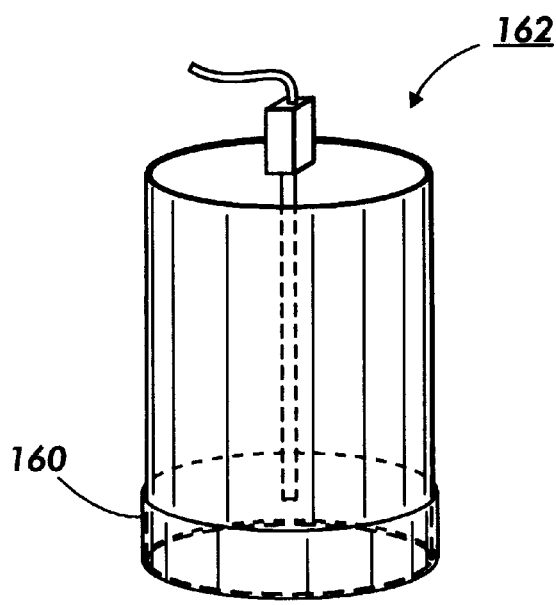
FIG. 11 is a schematic sectional view of a scorotron charging device used in the scanner system of this invention.

In FIG. 11, a grid 160 is shown fastened to the charging end of a scorotron 162 for contrasting the uniformity in the presence of a scorotron 150. Information from both scorotron 150 and scorotron 162 are needed for investigations of uniformity of belts. For such investigations, the corotron 150 and scorotron 162 may be mounted side by side on translating annular platform ring 86 at the location of single pin central electrode charging device 90 (see FIGS. 2 and 3). The corotron 150 emphasizes photoreceptor nonuniformities because the corotron replicates local thickness and dark decay variations whereas a scorotron 162 reveals the benchmark level of uniform charging in an imaging machine which actually utilizes a scorotron. The grid 160 permits ions formed by the central pin electrode 164 to pass through the grid 162 to the photoreceptor surface (not shown). Any suitable grid may be utilized. Typical grids include parallel wires, screens, honeycomb structures, mesh, and the like. The grid typically comprises electrically conductive materials such as the metals described above with reference to the central electrode and concentric shield. Sufficient voltage is applied to the central pin electrode 164 to achieve air breakdown. Generally, the grid 162 is maintained at about 100 volts to about 200 volts higher than the voltage of the charge to be deposited on the photoreceptor surface. The grid determines the voltage formed on the photoreceptor surface. Thus, the higher the grid potential, the higher the charge deposited on the photoreceptor surface. The grid 162 promotes contrast uniformity.

Where a flexible electrostatographic imaging member is supported on a rotating mandrel, grounding or biasing of the ground plane of the photoreceptor may be facilitated by utilizing an optional electrically conductive grounding device 164 see FIG. 2) in contact with a ground strip 166 which is usually located along at least one edge of the flexible electrostatographic imaging member or one edge of a rigid electrostatographic imaging drum. The grounding device 164 may comprise any suitable apparatus such as a conductive carbon fiber brush 168, electrically conductive rollers (not shown), a flexible conductive stylus (not shown), and the like. The electrical grounding device 164 may be cammed, pivoted or reciprocated into and away by any suitable device from the ground strip to facilitate mounting of the photoreceptor onto the mandrel. Alternatively, if mandrel 100 is grounded then the photoreceptor ground plane can be connected to the drum with an electrically conductive tape or other suitable device.

Electrophotographic (e.g. photoreceptor) flexible belt and rigid drum imaging members are well known in the art. They may comprise one or more electrically operative layers usually supported on a substrate. Typical examples of photosensitive members having at least two electrically operative layers including a charge generator layer and charge transport layer are disclosed in U.S. Pat. Nos. 4,265,990, 4,233,384, 4,306,008, 4,299,897 and 4,439,507. The disclosures of these patents are incorporated herein in their entirety.

The advantages of this invention include more uniform and stable levels of charging from one end of a belt or drum to the other during electronic mapping for a more accurate map of the charged surface of an electrophotographic imaging member. The expression "stable charging" is intended to describe the desired property of a charging device that provides a fixed level of charge in magnitude as well as in spatial content during the scan of entire belt. The charging devices of this invention provide between about 500 volts and about 1000 volts of charge on the imaging surface with a uniformity of about 1 volt and a resolution of about 1 millimeter. The scanner of this invention can determine with a high degree of precision the uniformity of thickness and charge on photoreceptors for precision imaging systems. The charging profiles obtained with the single pin central electrode charging device of this invention also have consistent and an almost gaussian shape which remains very stable.

The scanning system of this invention may also be utilized to scan and digitize electrostatic latent images carried by imaging members. The electrostatic latent images may be formed on the imaging members by any suitable technique. Typical techniques for forming electrostatic latent images include, for example, electrophotographic processes and electrographic methods. In electrophotographic processes, a photoconductive imaging member is uniformly charged in the dark and thereafter exposed to activating radiation in image configuration thereby selectively discharging the photoreceptor to form the electrostatic latent image. The photoconductive imaging member may be of any suitable type comprising photoconductive material that is sensitive to activating radiation such as infrared radiation, visible light, X-rays, ultraviolet radiation, and the like. Electrographic latent images are formed on dielectric imaging members using suitable imagewise charging devices such as shaped electrodes, styli, stencils, ion streams and the like. The electrostatic latent image (e.g., comprising a pattern of charged areas and areas having little or no charge) is scanned and converted to digital signals by the scanning system of this invention. The digitized signals representative of the electrostatic latent image may be stored and subsequently used for any suitable purpose such as producing a hard copy for diagnostic purposes in case of X-ray imaging, processing with pattern recognition software, detection of image defects, electronic manipulation, and the like

PREFERRED EMBODIMENTS OF THE INVENTION

A number of examples are set forth hereinbelow and are illustrative of different compositions and conditions that can be utilized in practicing the invention. All proportions are by weight unless otherwise indicated. It will be apparent, however, that the invention can be practiced with many types of compositions and can have many different uses in accordance with the disclosure above and as pointed out hereinafter.

EXAMPLE I

A scanning process was carried out in a scanner similar to that illustrated in FIGS. 2 and 3. A photoreceptor belt having a circumference of 679 cm and a width of 35.4 cm was mounted on a supporting rigid drum using compressed air in a manner similar to that illustrated in FIG. 4. The resulting assembly was mounted on a rotatable stage (Model ADR 220-5, available from Aerotech) with the drum axis aligned vertically. The drum was rotated at 99 rpm so that a complete revolution occurred in 0.606 second. A ring carrying the components illustrated in FIGS. 2 and 3 was translated from one end of the assembly to the other with a vertical stage (Model ATS500045, available from Aerotech) at a rate of 0.05 millimeter/revolution. The charging corotron mounted on the ring had a configuration similar to that illustrated in FIG. 10. The corotron comprised single pin central electrode having a diameter of 100 micrometers surrounded by a concentric shield electrode having an outside diameter of 1.5 cm centimeters and a thickness of 0.5 millimeter. The distance between the bottom of the shield and the outer surface of the photoreceptor belt was 1 millimeter. The distance from the charging end of the central pin electrode and the imaging surface of the photoreceptor was 4 millimeters. The central electrode and shield material were electrically conductive material, namely platinum for the center electrode and stainless steel for the shield. A voltage of 6 kilovolts was applied to the central electrode to achieve air breakdown. The ring also carried an electrostatic voltmeter probe (Model 369, available from Trek). The voltmeter probe was spaced 500 micrometers from the photoreceptor. Since the drum carrying the photoreceptor belt is constantly rotating, the probe path along the surface of the photoreceptor has, in essence, a helical shape. In the process of this Example, there were two main sources of noise frequency. One source was a 60 Hz line noise and the other source was a noise frequency at 682 Hz arising from the electrostatic voltmeter.

| Given Parameters: | |
| --- | --- |
| Rotational Speed | R = 99 rpm |
| Noise Frequency #1 | $N_1$ = 60 Hz |
| Noise Frequency #2 | $N_2$ = 682 Hz |

For example, for a predetermined rotational speed of 99 RPM with PHASE STEPPED NOISE REDUCTION optimized for noise frequencies of 60 Hz and 682 Hz, Referring to flow diagram illustrated in FIG. 9, the input including parameters R, $N_1$ and $N_2$ is represented by the first box in the flow diagram.

Number of noise cycles per revolution was:

| $L_1$ = [(60 s/minute) $N_1$]/R | $L_1$ = 36.36364 |
| --- | --- |
| $L_2$ = [(60 s/minute) $N_2$]/R | $L_2$ = 413.3333 |

This calculation is represented by the second box in the flow diagram.

Number of complete noise cycles per revolution was:

$C_1 = 36$ $C_2 = 413$

This determination is represented by the third box in the flow diagram.

Fractional amount of noise cycle remaining or left-over per cycle was:

| $P_1 = L_1 - C_1$ | $P_1 = 0.36364$ | $P_1 = 4/11$ |
| --- | --- | --- |
| $P_2 = L_2 - C_2$ | $P_2 = 0.3333$ | $P_2 = 1/3$ |

These calculations are represented by the fourth and fifth boxes in the flow diagram.

Number of points that must be averaged to eliminate the noise frequency, Ni was:

| $S_1$ = Denominator of $P_1$ | $S_1$ = 11 |
| --- | --- |
| $S_2$ = Denominator of $P_2$ | $S_2$ = 3 |

These calculations are represented by the sixth box in the flow diagram.

After the first set of calculations for $N_1$, $L_1$, $C_1$, $P_1$, and $S_1$, the diamond shaped box represents the decision to conduct a second set of calculations for $N_2$, $L_2$, $C_2$, $P_2$, and $S_2$.

After the series of calculations for $N_2$, $L_2$, $C_2$, $P_2$, and $S_2$, a decision is made as to whether to continue to the eighth box.

The number of points that should be averaged to eliminate all noise frequencies:

Q=Least Common Multiple of $S_1$ and $S_2$

Q=33

This calculation is represented by the eighth box in the flow diagram shown in FIG. 10.

EXAMPLE II

The procedures with the apparatus described in Example I were repeated, except the rotational speed was calculated for other noise frequencies. More specifically, for a predetermined rotational speed of 98 RPM with Phase Stepped Noise Reduction optimized for noise frequencies of 60 Hz, 120 Hz, and 701 Hz, Rotational Speed
R = 98 rpm
Noise Frequency #1
$N_1$ = 60 Hz
Noise Frequency #2
$N_2$ = 120 Hz
Noise Frequency #3
$N_3$ = 701 Hz -continued Number of noise cycles per revolution:

$L_1 = [(60 \text{ s/minute}) N_1]/R$
$L_1 = [(60 \text{ s/minute}) (60/s)]/(98/\text{minute})$
$L_1 = 36.7347$
$L_2 = ((60 \text{ s/minute}) N_2)/R$
$L_2 = [(60 \text{ s/minute}) (120/s)]/(98/\text{minute})$
$L_2 = 73.4694$
$L_3 = ((60 \text{ s/minute}) N_3)/R$
$L_3 = [(60 \text{ s/minute}) (701/s)]/(98/\text{minute})$
$L_3 = 429.1837$ Number of complete noise cycles per revolution:

$C_1 = 36$
$C_2 = 73$
$C_3 = 429$

Fractional amount of noise cycle left-over per cycle $P_1 = L_1 - C_1$
$P_1 = 36.7437 - 36$
$P_1 = 0.7437$
$P_1 = 36/49$
$P_2 = 73.4694 - 73$
$P_2 = 0.4694$
$P_2 = 23/49$
$P_3 = L_3 - C_3$
$P_3 = 429.1837 - 429$
$P_3 = 0.1837$
$P_3 = 9/49$ Number of points that must be averaged to eliminate the noise frequency, $N_i$:

$S_1 = $ Denominator of $P_1$
$S_1 = 49$
$S_2 = $ Denominator of $P_2$
$S_2 = 49$
$S_3 = $ Denominator of $P_3$
$S_3 = 49$ Number of points that must be averaged to eliminate all noise frequencies:

$Q = $ Least Common Multiple of $S_1$ and $S_2$ and $S_3$
$Q = 49$

Thus, a drum speed can be selected which is optimized for Phase Stepped Noise Reduction of 60 Hz noise, 120 Hz noise and 701 Hz noise. Other frequencies can be eliminated or reduced in a similar fashion.

EXAMPLE III

A flexible three pitch photoreceptor belt comprising a substrate, charge generating layer and charge transport layer and having an outer circumference of 67.93 cm and a width of 35.0 cm was pneumatically mounted on a vertical cylindrical mandrel, the lower end of the mandrel being secured to a rotary stage (Model ADR 200-5, available from Aerotech) in a system similar to the arrangement illustrated in FIG. 2. The mounted belt was rotated by the rotary stage at a constant speed of 100 RPM. A charging device and a high resolution scanning probe were mounted on an annular platform ring, the ring being concentric with the mounted belt. The ring was supported by and moved vertically by a vertical translation stage (Model ATS500045, available from Aerotech). The distances of the charging device and the probe from the photoreceptor imaging surface was maintained within 7 micrometers during the entire scan the belt. Three different runs were made using three different charging devices. The first charging device contained a 24 pin array in a rectangular shield in which the pins were evenly spaced in a row with a spacing of 3 millimeters between each pin. Each pin had a diameter of 100 micrometers. A rectangular conductive shield shielded the sides of the charging device. The interior surface of the sides of the shield was 10 millimeters from the closest pin. The shield was grounded through a feed back path. The second charging device contained an 8 pin array in which the pins were evenly spaced in a row with a spacing of 3 millimeters between each pin. Each pin had a diameter of 100 micrometers. A rectangular conductive shield shielded the sides of the charging device. The interior surface of the sides of the shield was 10 millimeters from the closest pin. The shield was grounded through a feed back path. The third charging device contained a single central pin having a diameter of 100 micrometers. A cylindrical conductive shield was positioned concentric ith the single central pin electrode. The interior surface of the shield was 5 millimeters from the pin. The shield was grounded through a feed back path.

Figure 12:
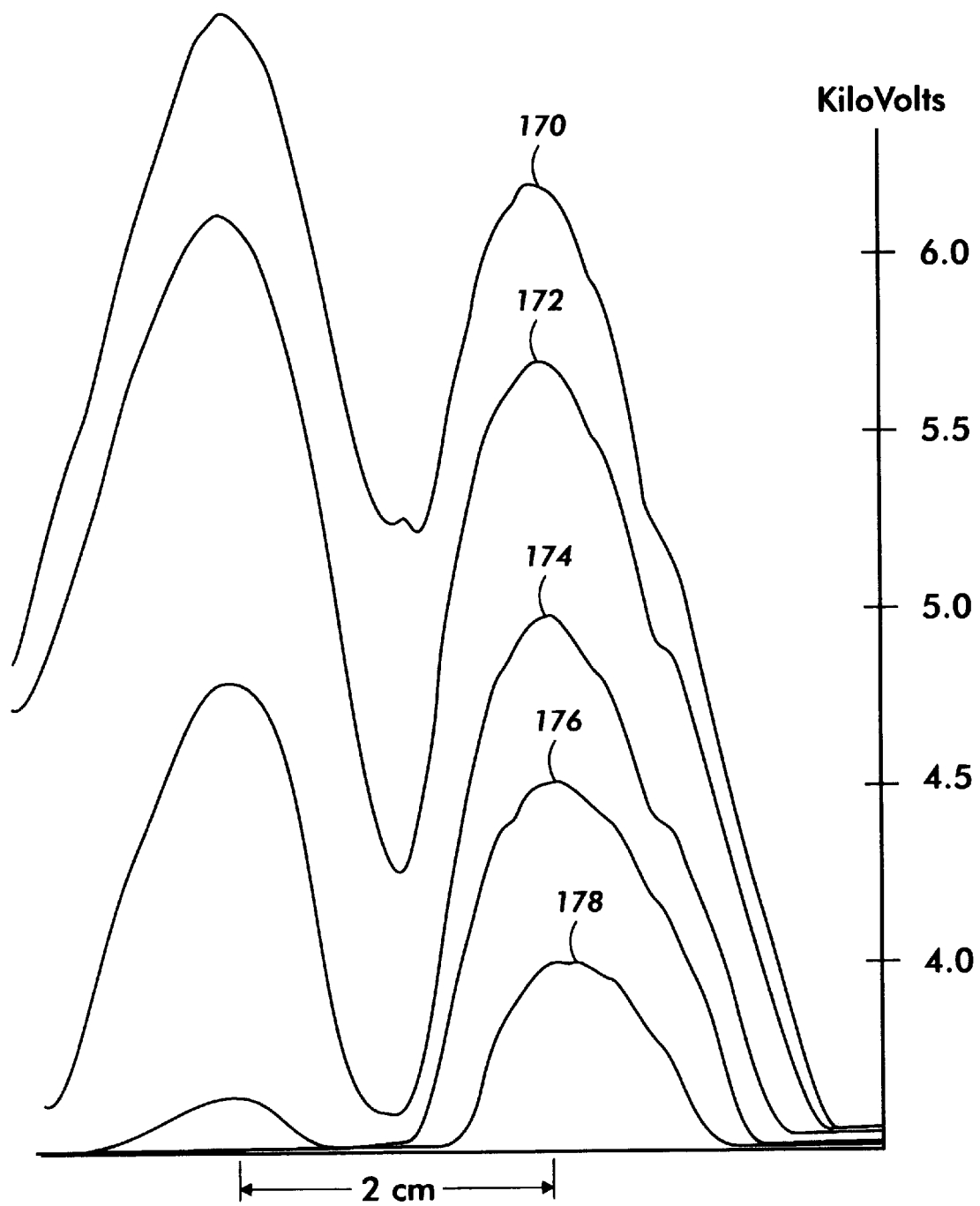
FIGS. 12 through 14 are scanner probe views of the charge pattern profiles deposited at various voltages applied to the pins of various corotrons.
Figure 13:
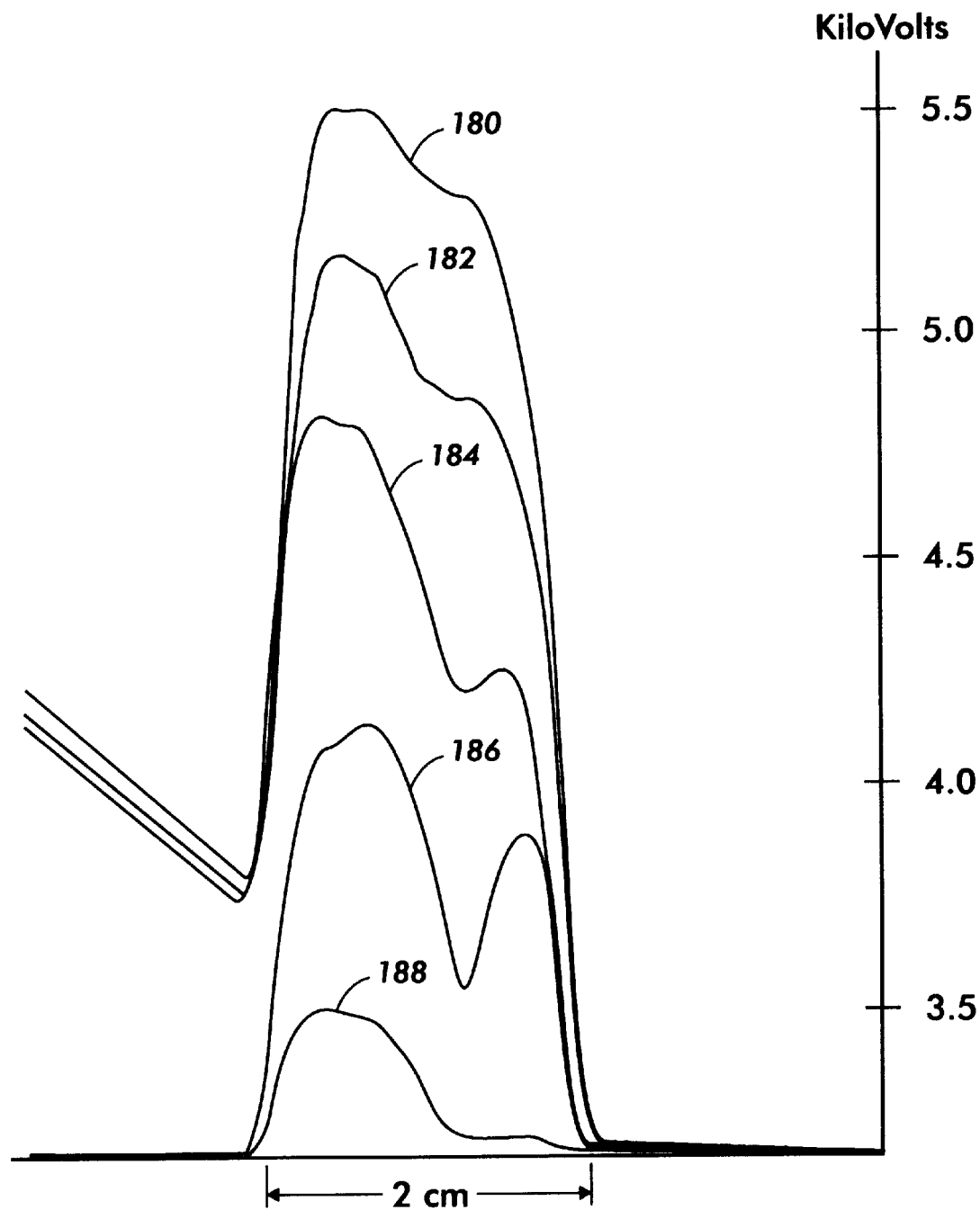
Figure 14:
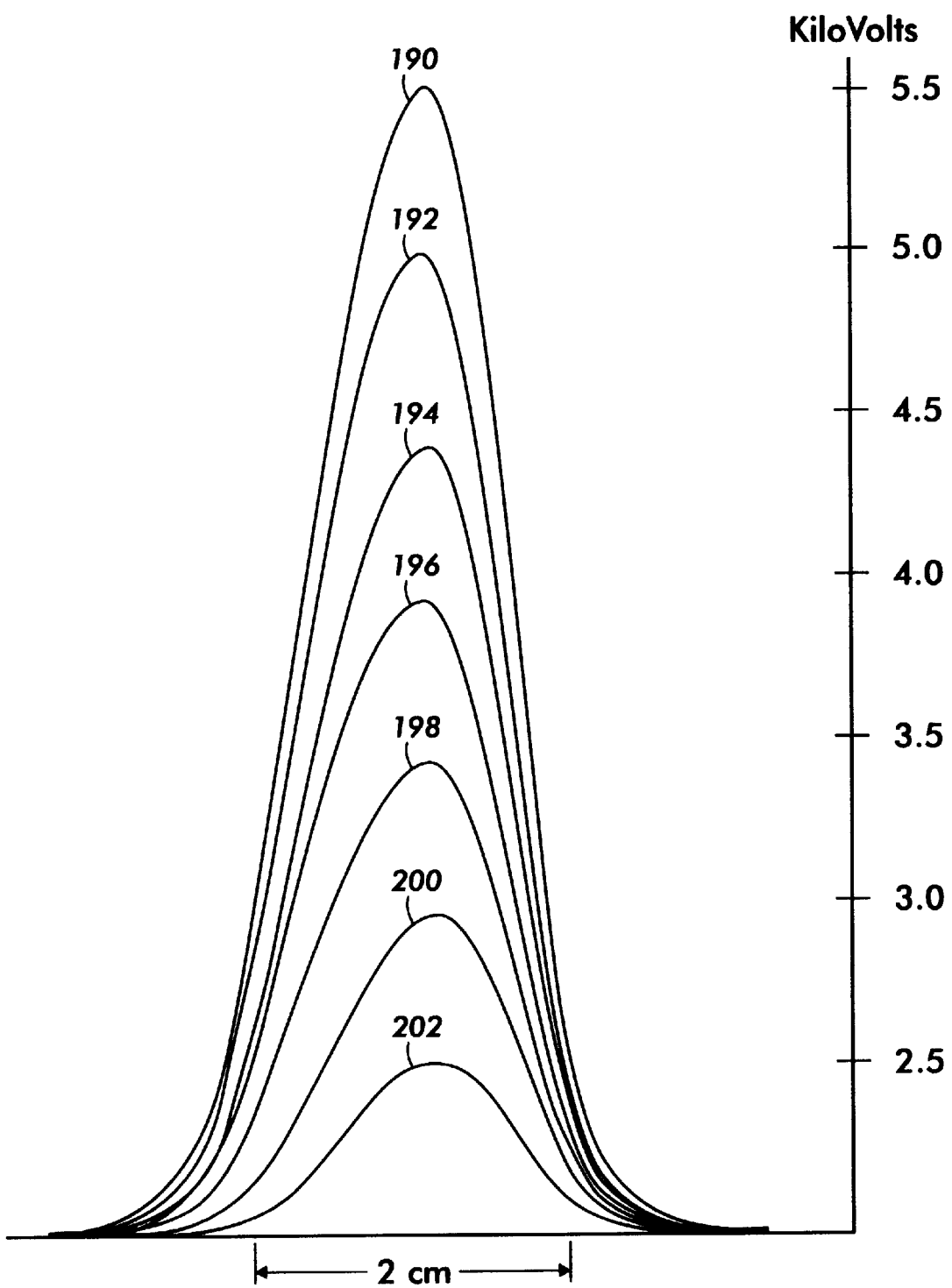

High resolution scanning probe views were plotted of charge pattern profiles deposited at various voltages applied to the pins of the three charging devices. FIG. 12 shows charging profiles for a 24 pin array where the profiles 170, 172, 174, 176, and 178 are formed with pin voltages of 6 kilovolts, 5.5 kilovolts, 5 kilovolts, 4.5 kilovolts and 4 kilovolts, respectively. FIG. 13 shows charging profiles for an 8 pin array where the profiles 180, 182, 184, 186, and 188 are formed with pin voltages of 5.5 kilovolts, 5 kilovolts, 4.5 kilovolts, 4 kilovolts and 3.5 kilovolts, respectively. FIG. 14 shows charging profiles for a single central pin electrode where the profiles 190, 192, 194, 196, 198, 200 and 20 are formed with pin voltages of 5.5 kilovolts, 5 kilovolts, 4.5 kilovolts, 4 kilovolts, 3.5 kilovolts, 3 kilovolts, and 2.5 kilovolts, respectively. In FIG. 12, the charging profile of a multi-pin corotron array is spatially very nonuniform. FIG. 13 shows the voltage profile change with changes in the applied voltage to the pins. FIG. 14 demonstrates that a single pin central electrode corotron charging device produces the most consistent shape. A small shift in the peak position is noted in the curves. This is due to the geometry of the corotron (1 inch wide, 2 inches long and 1 inch high) used in the investigation and a possible slight misalignment. For example, the pin may not have been equidistant from the two shield walls. A shield perfectly concentric with the single pin center electrode avoids this problem. The high resolution scanning probe on the ring is aligned with a peak of the charging profile produced by the single pin central electrode corotron in the scanning system of this invention. It is clear that variations in charging profiles of charges laid down with multiple pin or other conventional corotrons will fail to produce a reproducible high resolution electronic scanning map. The charging profiles obtained with the single pin central electrode charging device of this invention have an almost gaussian shape which remained very stable. The scanning system of this invention emphasizes photoreceptor nonuniformities because the narrow band of deposited charge replicates the local coating thickness variations as well as dark decay variations and can be accurately scanned to produce a repeatable high resolution electronic scanning map while avoiding photoreceptor fatigue during mapping.

Although the concentric single pin corotron gave a desired uniform charging any other suitable configuration may be used such as, for example, brush charging, biased roll charging, acquatron charging, charging corotron or scorotron with rectangular geometry with a suitable pin configuration, and the like.

EXAMPLE IV

The procedures with the apparatus described in Example I were repeated for a photoreceptor mounted on the apparatus. The voltage profiles were obtained in three different scans. From these scans, voltage patterns were obtained on the identical circumferential path. The patterns obtained matched perfectly within 0.5 volt at every point along the circumferential path. The same results were achieved for every other paths.

Although the invention has been described with reference to specific preferred embodiments, it is not intended to be limited thereto, rather those having ordinary skill in the art will recognize that variations and modifications may be made therein which are within the spirit of the invention and within the scope of the claims.

What is claimed is:

1. A contactless process for detecting surface potential charge patterns on the outer surface of a member comprising providing an electrostatographic imaging member having a charge pattern comprising selected multiple different time dependent noise signals, each having a frequency remaining constant in time, on an outer surface, repetitively measuring the charge pattern by oversampling spatially on the outer surface of the member with an electrostatic voltmeter probe maintained at a substantially constant distance from the surface, the distance between the probe and the imaging member being slightly greater than the minimum distance at which Paschen breakdown will occur to form a parallel plate capacitor with a gas between the probe and the surface, the frequency of repetition being selected to cause all the selected multiple different time dependent noise signals, each having a frequency remaining constant in time, to fall out of phase by a predetermined amount of phase, and averaging the out of phase selected multiple different time dependent noise signals, each having a frequency remaining constant in time, over a sufficient number of measuring repetitions to eliminate all the selected multiple different time noise dependent signals, each having a frequency remaining constant in time.

2. A contactless process for detecting surface potential charge patterns in an electrostatographic imaging member comprising
   providing a cylindrical electrostatographic imaging member having an outer imaging surface and an imaginary axis,
   providing an electrostatic voltmeter probe having a charge measuring end spaced from the outer imaging surface,
   maintaining the distance between the charge measuring end of the probe and the imaging surface substantially constant, the distance between the charge measuring end and the imaging member being slightly greater than the minimum distance at which Paschen breakdown will occur to form a parallel plate capacitor with a gas between the probe and the imaging surface,
   establishing relative movement between the probe and the imaging surface,
   depositing a charge on the imaging surface along a narrow predetermined path immediately prior to relative movement of the probe over the charge on the imaging surface, the deposited charge having a surface potential pattern containing low resolution variations having of a width of between about 0.1 millimeter and about 5 millimeters,
   repetitively measuring the deposited charge on the imaging surface with the electrostatic voltmeter probe, the frequency of repetition being selected to cause all time dependent signals to fall out of phase by a predetermined amount after each revolution, and
   averaging the out of phase time dependent signals over a sufficient number of measuring repetitions to eliminate the time dependent signals to detect the low resolution variations in the surface potential charge pattern.

3. A contactless process according to claim 2 wherein the charge is applied only along the narrow path on the imaging surface with a corotron or scorotron charging device, the charging device comprising a single pin central electrode and a concentric shield electrode, the central electrode having an axis positioned radially to the imaginary axis of the cylindrical imaging member and having a charging end spaced from the imaging surface.

4. A contactless process according to claim 3 wherein the predetermined narrow path of charge has a width of between about 5 millimeters and about 20 millimeters.

5. A contactless process according to claim 3 wherein the single pin central electrode has a diameter between about 10 micrometers and about 500 micrometers.

6. A contactless process according to claim 3 wherein the single pin central electrode has an outer surface spaced from the concentric shield electrode by a distance of between about 5 millimeters and about 30 millimeters.

7. A contactless process according to claim 3 wherein the single pin central electrode is spaced between about 1 millimeter and about 10 millimeters from the imaging surface.

8. A contactless process according to claim 2 wherein the electrostatographic member is a flexible belt.

9. A contactless process according to claim 8 including mounting the flexible belt on a rigid cylindrical mandrel prior to establishing the relative movement between the probe and the imaging surface.

10. A contactless process according to claim 9 including mounting the flexible belt on the rigid cylindrical mandrel by sliding the belt onto the mandrel while maintaining a film of air between the mandrel and the belt.

11. A contactless process for detecting thickness profiles in an electrostatographic imaging member comprising
   providing a cylindrical electrostatographic imaging member having an imaging layer having an outer imaging surface and an imaginary axis,
   providing an electrostatic voltmeter probe having a charge measuring end spaced from the outer imaging surface,
   maintaining the distance between the charge measuring end of the probe and the imaging surface substantially constant, the distance between the charge measuring end and the imaging member being slightly greater than the minimum distance at which Paschen breakdown will occur to form a parallel plate capacitor with a gas between the probe and the imaging surface,
   establishing relative movement between the probe and the imaging surface,
   depositing a charge on the imaging surface along a narrow predetermined path by a corotron in which the current through the imaging layer is held fixed by a feedback control system immediately prior to relative movement of the probe over the charge on the imaging surface, the deposited charge having a surface potential pattern replicating the thickness profile of imaging layer containing low resolution variations having of a width of between about 0.1 millimeter and about 5 millimeters, repetitively measuring the deposited charge on the imaging surface by the electrostatic voltmeter probe, the frequency of repetition being selected to cause all time dependent signals to fall out of phase by a predetermined amount after each revolution, and averaging the out of phase time dependent signals over a sufficient number of measuring repetitions to eliminate the time dependent signals to detect the low resolution variations in the surface potential thickness profiles in the electrostatographic imaging member charge pattern.

12. A contactless scanning system comprising a device to support and rotate a cylindrically shaped electrostatographic member having an imaging surface, a charging device adapted to deposit a charge on the imaging surface along a predetermined narrow path, an electrostatic voltmeter probe adjacent to and spaced from the imaging surface to form a parallel plate capacitor with the surface, a device adapted to position the charging device and the probe on the narrow path, the charging device comprising a central pin electrode and a concentric shield electrode, the central pin electrode having an axis positioned substantially perpendicular to the imaging surface.

13. A contactless scanning system according to claim 12 wherein the narrow path circumscribes the cylindrical shaped electrostatographic member.

14. A contactless scanning system according to claim 12 wherein the device to support the electrostatographic member is a mandrel.

15. A contactless scanning system according to claim 12 wherein the device to support the electrostatographic member is an expandable mandrel.

16. A contactless scanning system according to claim 12 wherein the device to support the electrostatographic member is rigid cylindrical mandrel having air holes adapted to expand a flexible electrostatographic belt.

* * * * *